US011730706B1

(12) United States Patent
Tabuteau

(10) Patent No.: US 11,730,706 B1
(45) Date of Patent: Aug. 22, 2023

(54) TREATMENT OF DEPRESSION IN CERTAIN PATIENT POPULATIONS

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

(*) Notice: Subject to any disclaimer, the term of this patent is extended or adjusted under 35 U.S.C. 154(b) by 0 days.

(21) Appl. No.: 18/158,268

(22) Filed: Jan. 23, 2023

Related U.S. Application Data

(60) Provisional application No. 63/359,143, filed on Jul. 7, 2022, provisional application No. 63/370,592, filed on Aug. 5, 2022, provisional application No. 63/396,182, filed on Aug. 8, 2022, provisional application No. 63/373,040, filed on Aug. 19, 2022, provisional application No. 63/401,541, filed on Aug. 26, 2022.

(51) Int. Cl.
*A61K 31/137* (2006.01)
*A61P 25/24* (2006.01)
*A61K 9/20* (2006.01)
*A61K 31/485* (2006.01)

(52) U.S. Cl.
CPC .......... *A61K 31/137* (2013.01); *A61K 9/2086* (2013.01); *A61K 31/485* (2013.01); *A61P 25/24* (2018.01)

(58) Field of Classification Search
CPC ...... A61K 31/137; A61K 31/485; A61P 25/24
See application file for complete search history.

(56) References Cited

U.S. PATENT DOCUMENTS

| | | | |
|---|---|---|---|
| 2,676,177 A | 4/1954 | Schnider et al. |
| 3,819,706 A | 6/1974 | Mehta |
| 4,687,660 A | 8/1987 | Baker et al. |
| 5,166,207 A | 11/1992 | Smith |
| 5,206,248 A | 4/1993 | Smith |
| 5,350,756 A | 9/1994 | Smith |
| 6,034,091 A | 3/2000 | Dante |
| 6,197,830 B1 | 3/2001 | Frome |
| 6,207,674 B1 | 3/2001 | Smith |
| 6,333,332 B1 | 12/2001 | Han et al. |
| 6,342,496 B1 | 1/2002 | Jerussi et al. |
| 6,436,938 B1 | 8/2002 | Howard |
| 6,458,374 B1 | 10/2002 | McCullough et al. |
| 6,562,835 B1 | 5/2003 | Caruso |
| 6,608,073 B1 | 8/2003 | Hussain et al. |
| 6,780,871 B2 | 8/2004 | Glick et al. |
| 6,897,241 B2 | 5/2005 | Frome |
| 7,569,610 B2 | 8/2009 | Oberegger et al. |
| 7,569,611 B2 | 8/2009 | Oberegger et al. |
| 7,579,380 B2 | 8/2009 | Oberegger et al. |
| 7,659,282 B2 | 2/2010 | Yakatan et al. |
| 7,674,479 B2 | 3/2010 | Zerbe et al. |
| 7,884,136 B2 | 2/2011 | Oberegger et al. |
| 7,973,043 B2 | 7/2011 | Migaly |
| 7,973,049 B2 | 7/2011 | Tung |
| 8,017,623 B2 | 9/2011 | Singh |
| 8,188,110 B2 | 5/2012 | Tung |
| 8,227,484 B2 | 7/2012 | Yakatan et al. |
| 8,461,102 B2 | 6/2013 | Royster |
| 8,524,780 B2 | 9/2013 | Czarnik |
| 8,541,436 B2 | 9/2013 | Tung |
| 8,569,328 B1 | 10/2013 | Tabuteau |
| 8,728,528 B2 | 5/2014 | Biggs et al. |
| 8,796,302 B2 | 8/2014 | Hong et al. |
| 8,932,628 B2 | 1/2015 | Oberegger et al. |
| 9,168,234 B2 | 10/2015 | Tabuteau |
| 9,198,905 B2 | 12/2015 | Tabuteau |
| 9,205,083 B2 | 12/2015 | Tabuteau |
| 9,238,032 B2 | 1/2016 | Tabuteau |
| 9,278,095 B2 | 3/2016 | Tabuteau |
| 9,314,462 B2 | 4/2016 | Tabuteau |
| 9,370,513 B2 | 6/2016 | Tabuteau |
| 9,375,429 B2 | 6/2016 | Tabuteau |

(Continued)

FOREIGN PATENT DOCUMENTS

| | | |
|---|---|---|
| AU | 2015350559 B2 | 12/2018 |
| EP | 1224930 | 7/2002 |

(Continued)

OTHER PUBLICATIONS

US 11,123,342 B2, 09/2021, Tabuteau (withdrawn)
Zarate Jr. et al., A Double-Blind, Placebo-Controlled Study of Memantine in the Treatment of Major Depression, American Journal of Psychiatry, 163(1), 153-155, Jan. 2006.
Ferguson et al., An open-label, flexible-dose study of memantine in major depressive disorder, Clinical Neuropharmacology, 30(3), 136-144, May 2007.
Chou et al., Binding of dimemorfan to sigma-1 receptor and its anticonvulsant and locomotor effects in mice, compared with dextromethorphan and dextrorphan, Brain research, 821(2), 516-519, Mar. 1999.
Foley et al., Bupropion: pharmacology and therapeutic applications, Expert review of neurotherapeutics, 6(9), 1249-1265, Sep. 2006.

(Continued)

*Primary Examiner* — Kevin E Weddington
(74) *Attorney, Agent, or Firm* — Maschoff Brennan; Brent A. Johnson; Yuefen Zhou

(57) ABSTRACT

This disclosure relates to administration of a combination of: 1) about 100-110 mg, about 104-106 mg, or about 105 mg of bupropion hydrochloride, or a molar equivalent amount of a free base form or another salt form of bupropion; and 2) about 40-50 mg, about 44-46 mg, or about 45 mg of dextromethorphan hydrobromide, or a molar equivalent amount of a free base form or another salt form of dextromethorphan in certain patient populations, such as patients having moderate renal impairment, patients receiving a concomitant strong CYP2D6 inhibitor, patients who are known CYP2D6 poor metabolizers, those in need of an NMDA antagonist that does not cause dissociation, and those at risk of QT prologation.

20 Claims, 1 Drawing Sheet

(56) References Cited

U.S. PATENT DOCUMENTS

| | | |
|---|---|---|
| 9,402,843 B2 | 8/2016 | Tabuteau |
| 9,402,844 B2 | 8/2016 | Tabuteau |
| 9,408,815 B2 | 8/2016 | Tabuteau |
| 9,421,176 B1 | 8/2016 | Tabuteau |
| 9,457,023 B1 | 10/2016 | Tabuteau |
| 9,457,025 B2 | 10/2016 | Tabuteau |
| 9,474,731 B1 | 10/2016 | Tabuteau |
| 9,486,450 B2 | 11/2016 | Tabuteau |
| 9,700,528 B2 | 7/2017 | Tabuteau |
| 9,700,553 B2 | 7/2017 | Tabuteau |
| 9,707,191 B2 | 7/2017 | Tabuteau |
| 9,732,031 B2 | 8/2017 | DeWitt et al. |
| 9,763,932 B2 | 9/2017 | Tabuteau |
| 9,861,595 B2 | 1/2018 | Tabuteau |
| 9,867,819 B2 | 1/2018 | Tabuteau |
| 9,968,568 B2 | 5/2018 | Tabuteau |
| 10,058,518 B2 | 8/2018 | Tabuteau |
| 10,064,857 B2 | 9/2018 | Tabuteau |
| 10,080,727 B2 | 9/2018 | Tabuteau |
| 10,092,560 B2 | 10/2018 | Tabuteau |
| 10,092,561 B2 | 10/2018 | Tabuteau |
| 10,105,327 B2 | 10/2018 | Tabuteau |
| 10,105,361 B2 | 10/2018 | Tabuteau |
| 10,251,879 B2 | 4/2019 | Tabuteau |
| 10,463,634 B2 | 11/2019 | Tabuteau |
| 10,512,643 B2 | 12/2019 | Tabuteau |
| 10,548,857 B2 | 2/2020 | Tabuteau |
| 10,596,167 B2 | 3/2020 | Tabuteau |
| 10,688,066 B2 | 6/2020 | Tabuteau |
| 10,695,304 B2 | 6/2020 | Tabuteau |
| 10,772,850 B2 | 9/2020 | Tabuteau |
| 10,780,064 B2 * | 9/2020 | Tabuteau ............... A61P 25/24 |
| 10,780,066 B2 | 9/2020 | Tabuteau |
| 10,786,469 B2 * | 9/2020 | Tabuteau ............... A61K 9/20 |
| 10,786,496 B2 | 9/2020 | Tabuteau |
| 10,799,497 B2 * | 10/2020 | Tabuteau ............ A61K 31/135 |
| 10,806,710 B2 | 10/2020 | Tabuteau |
| 10,813,924 B2 | 10/2020 | Tabuteau |
| 10,864,209 B2 | 12/2020 | Tabuteau |
| 10,874,663 B2 | 12/2020 | Tabuteau |
| 10,874,664 B2 | 12/2020 | Tabuteau |
| 10,874,665 B2 | 12/2020 | Tabuteau |
| 10,881,624 B2 | 1/2021 | Tabuteau |
| 10,881,657 B2 | 1/2021 | Tabuteau |
| 10,894,046 B2 * | 1/2021 | Tabuteau ............ A61K 31/343 |
| 10,894,047 B2 | 1/2021 | Tabuteau |
| 10,898,453 B2 | 1/2021 | Tabuteau |
| 10,925,842 B2 * | 2/2021 | Tabuteau ............ A61K 31/485 |
| 10,933,034 B2 | 3/2021 | Tabuteau |
| 10,940,124 B2 * | 3/2021 | Tabuteau ............ A61K 31/135 |
| 10,945,973 B2 | 3/2021 | Tabuteau |
| 10,966,941 B2 | 4/2021 | Tabuteau |
| 10,966,942 B2 * | 4/2021 | Tabuteau ............ A61K 31/138 |
| 10,966,974 B2 | 4/2021 | Tabuteau |
| 10,980,800 B2 | 4/2021 | Tabuteau |
| 11,007,189 B2 | 5/2021 | Tabuteau |
| 11,020,389 B2 | 6/2021 | Tabuteau |
| 11,058,648 B2 | 7/2021 | Tabuteau |
| 11,065,248 B2 | 7/2021 | Tabuteau |
| 11,090,300 B2 | 8/2021 | Tabuteau |
| 11,096,937 B2 | 8/2021 | Tabuteau |
| 11,123,343 B2 | 9/2021 | Tabuteau |
| 11,123,344 B2 | 9/2021 | Tabuteau |
| 11,129,826 B2 | 9/2021 | Tabuteau |
| 11,141,388 B2 * | 10/2021 | Tabuteau ............ A61K 31/138 |
| 11,141,416 B2 | 10/2021 | Tabuteau |
| 11,147,808 B2 | 10/2021 | Tabuteau |
| 11,185,515 B2 | 11/2021 | Tabuteau |
| 11,191,739 B2 * | 12/2021 | Tabuteau ............ A61K 9/0053 |
| 11,197,839 B2 | 12/2021 | Tabuteau |
| 11,207,281 B2 | 12/2021 | Tabuteau |
| 11,213,521 B2 | 1/2022 | Tabuteau |
| 11,229,640 B2 | 1/2022 | Tabuteau |
| 11,234,946 B2 | 2/2022 | Tabuteau |
| 11,253,491 B2 * | 2/2022 | Tabuteau ............ A61K 31/485 |
| 11,253,492 B2 | 2/2022 | Tabuteau |
| 11,273,133 B2 | 3/2022 | Tabuteau |
| 11,273,134 B2 | 3/2022 | Tabuteau |
| 11,285,118 B2 | 3/2022 | Tabuteau |
| 11,285,146 B2 | 3/2022 | Tabuteau |
| 11,291,638 B2 | 4/2022 | Tabuteau |
| 11,291,665 B2 | 4/2022 | Tabuteau |
| 11,298,351 B2 | 4/2022 | Tabuteau |
| 11,298,352 B2 | 4/2022 | Tabuteau |
| 11,311,534 B2 | 4/2022 | Tabuteau |
| 11,344,544 B2 | 5/2022 | Tabuteau |
| 11,357,744 B2 | 6/2022 | Tabuteau |
| 11,364,233 B2 | 6/2022 | Tabuteau |
| 11,382,874 B2 | 7/2022 | Tabuteau |
| 11,419,867 B2 | 8/2022 | Tabuteau |
| 11,426,370 B2 | 8/2022 | Tabuteau |
| 11,426,401 B2 | 8/2022 | Tabuteau |
| 11,433,067 B2 | 9/2022 | Tabuteau |
| 11,439,636 B1 | 9/2022 | Tabuteau |
| 11,478,468 B2 | 10/2022 | Tabuteau |
| 11,497,721 B2 | 11/2022 | Tabuteau |
| 11,510,918 B2 | 11/2022 | Tabuteau |
| 11,517,542 B2 | 12/2022 | Tabuteau |
| 11,517,543 B2 | 12/2022 | Tabuteau |
| 11,517,544 B2 | 12/2022 | Tabuteau |
| 11,524,007 B2 | 12/2022 | Tabuteau |
| 11,524,008 B2 | 12/2022 | Tabuteau |
| 11,534,414 B2 | 12/2022 | Tabuteau |
| 11,541,021 B2 | 1/2023 | Tabuteau |
| 11,541,048 B2 | 1/2023 | Tabuteau |
| 11,571,399 B2 | 2/2023 | Tabuteau |
| 11,571,417 B2 | 2/2023 | Tabuteau |
| 11,576,877 B2 * | 2/2023 | Tabuteau ............ A61K 31/135 |
| 11,576,909 B2 | 2/2023 | Tabuteau |
| 11,590,124 B2 | 2/2023 | Tabuteau |
| 11,617,728 B2 | 4/2023 | Tabuteau |
| 11,617,747 B2 | 4/2023 | Tabuteau |
| 11,628,149 B2 | 4/2023 | Tabuteau |
| 2002/0004078 A1 | 1/2002 | Gelber et al. |
| 2002/0035105 A1 | 3/2002 | Caruso |
| 2002/0103109 A1 | 8/2002 | Glick et al. |
| 2003/0144220 A1 | 7/2003 | Obach |
| 2004/0092511 A1 | 5/2004 | Billstein et al. |
| 2005/0085463 A1 | 4/2005 | Weiner et al. |
| 2005/0203125 A1 | 9/2005 | Yakatan et al. |
| 2005/0209218 A1 | 9/2005 | Meyerson et al. |
| 2005/0250767 A1 | 11/2005 | Weiner et al. |
| 2006/0167032 A1 | 7/2006 | Galer et al. |
| 2006/0258721 A1 | 11/2006 | Maddaford et al. |
| 2007/0027213 A1 | 2/2007 | Oberegger |
| 2007/0042969 A1 | 2/2007 | Rauschkolb-Loffler et al. |
| 2008/0008748 A1 | 1/2008 | Beyreuther et al. |
| 2008/0081072 A1 | 4/2008 | Cherukuri |
| 2008/0213217 A1 | 9/2008 | Storer et al. |
| 2008/0280936 A1 | 11/2008 | Tung |
| 2008/0286344 A1 | 11/2008 | Darmuzey et al. |
| 2009/0023744 A1 | 1/2009 | Fava |
| 2009/0111846 A1 | 4/2009 | Berg |
| 2009/0124583 A1 | 5/2009 | Nelson et al. |
| 2009/0162421 A1 | 6/2009 | Geisslinger et al. |
| 2009/0191257 A1 | 7/2009 | Smith |
| 2010/0029665 A1 | 2/2010 | Meyerson et al. |
| 2010/0040679 A1 | 2/2010 | Chang et al. |
| 2011/0039875 A1 | 2/2011 | Singh |
| 2011/0206780 A1 | 8/2011 | Gant et al. |
| 2011/0217371 A1 | 9/2011 | Shin et al. |
| 2011/0245208 A1 | 10/2011 | Diatchenko et al. |
| 2012/0053169 A1 | 3/2012 | Thomas |
| 2012/0083487 A1 | 4/2012 | Thomas |
| 2012/0252833 A1 | 10/2012 | Wertz et al. |
| 2013/0137714 A1 | 5/2013 | Berg |
| 2014/0018436 A1 | 1/2014 | Czarnik |
| 2014/0162965 A1 | 6/2014 | Maggio |
| 2015/0087669 A1 | 3/2015 | Lammert et al. |
| 2015/0126541 A1 | 5/2015 | Tabuteau |
| 2015/0126542 A1 | 5/2015 | Tabuteau |
| 2015/0126543 A1 | 5/2015 | Tabuteau |
| 2015/0126544 A1 | 5/2015 | Tabuteau |
| 2015/0133485 A1 | 5/2015 | Tabuteau |

(56) References Cited

U.S. PATENT DOCUMENTS

| | | |
|---|---|---|
| 2015/0133486 A1 | 5/2015 | Tabuteau |
| 2015/0150830 A1 | 6/2015 | Tabuteau |
| 2015/0157582 A1 | 6/2015 | Tabuteau |
| 2016/0008352 A1 | 1/2016 | Tabuteau |
| 2016/0030420 A1 | 2/2016 | Tabuteau |
| 2016/0030421 A1 | 2/2016 | Tabuteau |
| 2016/0128998 A1 | 5/2016 | Tabuteau |
| 2016/0136155 A1 | 5/2016 | Tabuteau |
| 2016/0143901 A1 | 5/2016 | Siffert et al. |
| 2016/0199321 A1 | 7/2016 | Tabuteau |
| 2016/0228390 A1 | 8/2016 | Tabuteau |
| 2016/0263099 A1 | 9/2016 | Tabuteau |
| 2016/0263100 A1 | 9/2016 | Tabuteau |
| 2016/0317475 A1 | 11/2016 | Tabuteau |
| 2016/0317476 A1 | 11/2016 | Tabuteau |
| 2016/0324807 A1 | 11/2016 | Tabuteau |
| 2016/0339017 A1 | 11/2016 | Tabuteau |
| 2016/0346276 A1 | 12/2016 | Tabuteau |
| 2016/0361305 A1 | 12/2016 | Tabuteau |
| 2016/0375008 A1 | 12/2016 | Tabuteau |
| 2016/0375012 A1 | 12/2016 | Tabuteau |
| 2017/0007558 A1 | 1/2017 | Tabuteau |
| 2017/0014357 A1 | 1/2017 | Tabuteau |
| 2017/0252309 A1 | 9/2017 | Tabuteau |
| 2017/0281617 A1 | 10/2017 | Tabuteau |
| 2017/0304229 A1 | 10/2017 | Tabuteau |
| 2017/0304230 A1 | 10/2017 | Tabuteau |
| 2017/0304298 A1 | 10/2017 | Tabuteau |
| 2017/0354619 A1 | 12/2017 | Tabuteau |
| 2017/0360773 A1 | 12/2017 | Tabuteau |
| 2017/0360774 A1 | 12/2017 | Tabuteau |
| 2017/0360776 A1 | 12/2017 | Tabuteau |
| 2018/0092906 A1 | 4/2018 | Tabuteau |
| 2018/0116980 A1 | 5/2018 | Tabuteau |
| 2018/0133195 A1 | 5/2018 | Tabuteau |
| 2018/0207151 A1 | 7/2018 | Tabuteau |
| 2018/0256518 A1 | 9/2018 | Tabuteau |
| 2018/0360823 A1 | 12/2018 | Tabuteau |
| 2019/0000835 A1 | 1/2019 | Tabuteau |
| 2019/0008800 A1 | 1/2019 | Tabuteau |
| 2019/0008801 A1 | 1/2019 | Tabuteau |
| 2019/0008805 A1 | 1/2019 | Tabuteau |
| 2019/0015407 A1 | 1/2019 | Tabuteau |
| 2019/0083426 A1 | 3/2019 | Tabuteau |
| 2019/0142768 A1 | 5/2019 | Tabuteau |
| 2019/0192450 A1 | 6/2019 | Tabuteau |
| 2019/0192507 A1 | 6/2019 | Tabuteau |
| 2019/0216798 A1 | 7/2019 | Tabuteau |
| 2019/0216800 A1 | 7/2019 | Tabuteau |
| 2019/0216801 A1 | 7/2019 | Tabuteau |
| 2019/0290601 A1 | 9/2019 | Tabuteau |
| 2020/0022929 A1 | 1/2020 | Tabuteau |
| 2020/0093762 A1 | 3/2020 | Tabuteau |
| 2020/0147008 A1 | 5/2020 | Tabuteau |
| 2020/0147075 A1 | 5/2020 | Tabuteau |
| 2020/0206217 A1 | 7/2020 | Tabuteau |
| 2020/0215055 A1 | 7/2020 | Tabuteau |
| 2020/0215056 A1 | 7/2020 | Tabuteau |
| 2020/0215057 A1 | 7/2020 | Tabuteau |
| 2020/0215058 A1 | 7/2020 | Tabuteau |
| 2020/0215059 A1 | 7/2020 | Tabuteau |
| 2020/0222389 A1 | 7/2020 | Tabuteau |
| 2020/0230078 A1 | 7/2020 | Tabuteau |
| 2020/0230129 A1 | 7/2020 | Tabuteau |
| 2020/0230130 A1 | 7/2020 | Tabuteau |
| 2020/0230131 A1 | 7/2020 | Tabuteau |
| 2020/0237751 A1 | 7/2020 | Tabuteau |
| 2020/0237752 A1 | 7/2020 | Tabuteau |
| 2020/0246280 A1 | 8/2020 | Tabuteau |
| 2020/0261431 A1 | 8/2020 | Tabuteau |
| 2020/0297666 A1 | 9/2020 | Tabuteau |
| 2020/0338022 A1 | 10/2020 | Tabuteau |
| 2020/0360310 A1 | 11/2020 | Tabuteau |
| 2020/0397723 A1 | 12/2020 | Tabuteau |
| 2020/0397724 A1 | 12/2020 | Tabuteau |
| 2020/0405664 A1 | 12/2020 | Tabuteau |
| 2021/0000763 A1 | 1/2021 | Tabuteau |
| 2021/0000764 A1 | 1/2021 | Tabuteau |
| 2021/0000765 A1 | 1/2021 | Tabuteau |
| 2021/0000768 A1 | 1/2021 | Tabuteau |
| 2021/0000820 A1 | 1/2021 | Tabuteau |
| 2021/0015768 A1 | 1/2021 | Tabuteau |
| 2021/0015814 A1 | 1/2021 | Tabuteau |
| 2021/0015815 A1 | 1/2021 | Tabuteau |
| 2021/0023075 A1 | 1/2021 | Tabuteau |
| 2021/0023076 A1 | 1/2021 | Tabuteau |
| 2021/0030747 A1 | 2/2021 | Tabuteau |
| 2021/0030749 A1 | 2/2021 | Tabuteau |
| 2021/0030750 A1 | 2/2021 | Tabuteau |
| 2021/0030751 A1 | 2/2021 | Tabuteau |
| 2021/0046067 A1 | 2/2021 | Tabuteau |
| 2021/0052521 A1 | 2/2021 | Tabuteau |
| 2021/0060004 A1 | 3/2021 | Tabuteau |
| 2021/0060005 A1 | 3/2021 | Tabuteau |
| 2021/0069125 A1 | 3/2021 | Tabuteau |
| 2021/0069128 A1 | 3/2021 | Tabuteau |
| 2021/0077428 A1 | 3/2021 | Tabuteau |
| 2021/0077429 A1 | 3/2021 | Tabuteau |
| 2021/0077483 A1 | 3/2021 | Tabuteau |
| 2021/0106546 A1 | 4/2021 | Tabuteau |
| 2021/0186899 A1 | 6/2021 | Tabuteau |
| 2021/0186900 A1 | 6/2021 | Tabuteau |
| 2021/0186901 A1 | 6/2021 | Tabuteau |
| 2021/0186955 A1 | 6/2021 | Tabuteau |
| 2021/0186956 A1 | 6/2021 | Tabuteau |
| 2021/0205239 A1 | 7/2021 | Tabuteau |
| 2021/0205240 A1 | 7/2021 | Tabuteau |
| 2021/0205297 A1 | 7/2021 | Tabuteau |
| 2021/0220293 A1 | 7/2021 | Tabuteau |
| 2021/0220294 A1 | 7/2021 | Tabuteau |
| 2021/0220348 A1 | 7/2021 | Tabuteau |
| 2021/0260054 A1 | 8/2021 | Tabuteau |
| 2021/0267967 A1 | 9/2021 | Tabuteau |
| 2021/0338605 A1 | 11/2021 | Tabuteau |
| 2021/0346370 A1 | 11/2021 | Tabuteau |
| 2021/0361645 A1 | 11/2021 | Tabuteau |
| 2021/0401828 A1 | 12/2021 | Tabuteau |
| 2021/0401829 A1 | 12/2021 | Tabuteau |
| 2021/0401830 A1 | 12/2021 | Tabuteau |
| 2021/0401831 A1 | 12/2021 | Tabuteau |
| 2022/0008363 A1 | 1/2022 | Tabuteau |
| 2022/0071930 A1 | 3/2022 | Tabuteau |
| 2022/0071931 A1 | 3/2022 | Tabuteau |
| 2022/0079892 A1 | 3/2022 | Tabuteau |
| 2022/0096462 A1 | 3/2022 | Tabuteau |
| 2022/0105086 A1 | 4/2022 | Tabuteau |
| 2022/0133655 A1 | 5/2022 | Tabuteau |
| 2022/0142950 A1 | 5/2022 | Tabuteau |
| 2022/0193012 A1 | 6/2022 | Tabuteau |
| 2022/0218631 A1 | 7/2022 | Tabuteau |
| 2022/0218698 A1 | 7/2022 | Tabuteau |
| 2022/0233470 A1 | 7/2022 | Tabuteau |
| 2022/0233474 A1 | 7/2022 | Tabuteau |
| 2022/0233518 A1 | 7/2022 | Tabuteau |
| 2022/0233519 A1 | 7/2022 | Tabuteau |
| 2022/0241220 A1 | 8/2022 | Tabuteau |
| 2022/0241221 A1 | 8/2022 | Tabuteau |
| 2022/0241269 A1 | 8/2022 | Tabuteau |
| 2022/0241270 A1 | 8/2022 | Tabuteau |
| 2022/0265639 A1 | 8/2022 | Tabuteau |
| 2022/0280504 A1 | 9/2022 | Tabuteau |
| 2022/0313689 A1 | 10/2022 | Tabuteau |
| 2022/0323381 A1 | 10/2022 | Tabuteau |
| 2022/0378779 A1 | 12/2022 | Tabuteau |
| 2023/0045675 A1 | 2/2023 | Tabuteau |
| 2023/0096437 A1 | 3/2023 | Tabuteau |
| 2023/0099206 A1 | 3/2023 | Tabuteau |
| 2023/0100008 A1 | 3/2023 | Tabuteau |
| 2023/0100913 A1 | 3/2023 | Tabuteau |
| 2023/0114111 A1 | 4/2023 | Tabuteau |

(56) References Cited

U.S. PATENT DOCUMENTS

2023/0131854 A1    4/2023  Tabuteau
2023/0142244 A1    5/2023  Tabuteau

FOREIGN PATENT DOCUMENTS

| | | |
|---|---|---|
| EP | 2397158 | 12/2011 |
| EP | 2418211 | 2/2012 |
| WO | 1998050044 | 11/1998 |
| WO | 2000016762 | 3/2000 |
| WO | 2000041684 | 7/2000 |
| WO | 2000059486 | 10/2000 |
| WO | 2001045708 | 6/2001 |
| WO | 2002060425 | 8/2002 |
| WO | 2004075832 | 9/2004 |
| WO | 2006092691 | 9/2006 |
| WO | 2009006194 | 1/2009 |
| WO | 2009011412 | 1/2009 |
| WO | 2009062318 | 5/2009 |
| WO | 2009062319 | 5/2009 |
| WO | 2010000073 | 1/2010 |
| WO | 2010010343 | 1/2010 |
| WO | 2010062690 | 6/2010 |
| WO | 2010062692 | 6/2010 |
| WO | 2012118562 | 9/2012 |
| WO | 2012118563 | 9/2012 |
| WO | 2013136078 | 9/2013 |
| WO | 2013158680 | 10/2013 |
| WO | 2013190013 | 12/2013 |
| WO | 2014100501 | 6/2014 |
| WO | 2014138669 | 9/2014 |
| WO | 2015069809 A1 | 5/2015 |
| WO | 2015095713 | 6/2015 |

OTHER PUBLICATIONS

U.S. Appl. No. 16/894,713, filed Jun. 5, 2020 First Named Inventor: Herriot Tabuteau Assignee: Antecip Bioventures II LLC.
U.S. Appl. No. 16/926,458, filed Jul. 10, 2020 First Named Inventor: Herriot Tabuteau Assignee: Antecip Bioventures II LLC.
U.S. Appl. No. 16/983,873, filed Aug. 3, 2020 First Named Inventor: Herriot Tabuteau Assignee: Antecip Bioventures II LLC.
U.S. Appl. No. 17/002,017, filed Aug. 25, 2020 First Named Inventor: Herriot Tabuteau Assignee: Antecip Bioventures II LLC.
U.S. Appl. No. 17/003,777, filed Aug. 26, 2020 First Named Inventor: Herriot Tabuteau Assignee: Antecip Bioventures II LLC.
U.S. Appl. No. 17/020,393, filed Sep. 14, 2020 First Named Inventor: Herriot Tabuteau Assignee: Antecip Bioventures II LLC.
U.S. Appl. No. 17/022,629, filed Sep. 16, 2020 First Named Inventor: Herriot Tabuteau Assignee: Antecip Bioventures II LLC.
U.S. Appl. No. 17/022,781, filed Sep. 16, 2020 First Named Inventor: Herriot Tabuteau Assignee: Antecip Bioventures II LLC.
U.S. Appl. No. 17/024,145, filed Sep. 17, 2020 First Named Inventor: Herriot Tabuteau Assignee: Antecip Bioventures II LLC.
U.S. Appl. No. 17/025,849, filed Sep. 18, 2020 First Named Inventor: Herriot Tabuteau Assignee: Antecip Bioventures II LLC.
U.S. Appl. No. 17/027,608, filed Sep. 21, 2020 First Named Inventor: Herriot Tabuteau Assignee: Antecip Bioventures II LLC.
U.S. Appl. No. 17/030,129, filed Sep. 23, 2020 First Named Inventor: Herriot Tabuteau Assignee: Antecip Bioventures II LLC.
U.S. Appl. No. 17/039,551, filed Sep. 30, 2020 First Named Inventor: Herriot Tabuteau Assignee: Antecip Bioventures II LLC.
U.S. Appl. No. 17/061,047, filed Oct. 1, 2020 First Named Inventor: Herriot Tabuteau Assignee: Antecip Bioventures II LLC.
U.S. Appl. No. 17/063,364, filed Oct. 5, 2020 First Named Inventor: Herriot Tabuteau Assignee: Antecip Bioventures II LLC.
U.S. Appl. No. 17/066,310, filed Oct. 8, 2020 First Named Inventor: Herriot Tabuteau Assignee: Antecip Bioventures II LLC.
U.S. Appl. No. 17/068,309, filed Oct. 12, 2020 First Named Inventor: Herriot Tabuteau Assignee: Antecip Bioventures II LLC.
U.S. Appl. No. 17/070,706, filed Oct. 14, 2020 First Named Inventor: Herriot Tabuteau Assignee: Antecip Bioventures II LLC.
U.S. Appl. No. 17/071,925, filed Oct. 15, 2020 First Named Inventor: Herriot Tabuteau Assignee: Antecip Bioventures II LLC.
U.S. Appl. No. 17/075,189, filed Oct. 20, 2020 First Named Inventor: Herriot Tabuteau Assignee: Antecip Bioventures II LLC.
U.S. Appl. No. 17/087,890, filed Nov. 3, 2020 First Named Inventor: Herriot Tabuteau Assignee: Antecip Bioventures II LLC.
U.S. Appl. No. 17/092,968, filed Nov. 9, 2020 First Named Inventor: Herriot Tabuteau Assignee: Antecip Bioventures II LLC.
U.S. Appl. No. 17/095,256, filed Nov. 11, 2020 First Named Inventor: Herriot Tabuteau Assignee: Antecip Bioventures II LLC.
U.S. Appl. No. 17/097,486, filed Nov. 13, 2020 First Named Inventor: Herriot Tabuteau Assignee: Antecip Bioventures II LLC.
U.S. Appl. No. 17/099,226, filed Nov. 16, 2020 First Named Inventor: Herriot Tabuteau Assignee: Antecip Bioventures II LLC.
U.S. Appl. No. 16/950,838, filed Nov. 17, 2020 First Named Inventor: Herriot Tabuteau Assignee: Antecip Bioventures II LLC.
U.S. Appl. No. 17/100,456, filed Nov. 20, 2020 First Named Inventor: Herriot Tabuteau Assignee: Antecip Bioventures II LLC.
U.S. Appl. No. 17/103,819, filed Nov. 24, 2020 First Named Inventor: Herriot Tabuteau Assignee: Antecip Bioventures II LLC.
U.S. Appl. No. 17/115,073, filed Dec. 8, 2020 First Named Inventor: Herriot Tabuteau Assignee: Antecip Bioventures II LLC.
U.S. Appl. No. 17/191,014, filed Mar. 3, 2021 First Named Inventor: Herriot Tabuteau Assignee: Antecip Bioventures II LLC.
U.S. Appl. No. 17/192,192, filed Mar. 4, 2021 First Named Inventor: Herriot Tabuteau Assignee: Antecip Bioventures II LLC.
U.S. Appl. No. 17/192,563, filed Mar. 4, 2021 First Named Inventor: Herriot Tabuteau Assignee: Antecip Bioventures II LLC.
U.S. Appl. No. 17/193,306, filed Mar. 5, 2021 First Named Inventor: Herriot Tabuteau Assignee: Antecip Bioventures II LLC.
U.S. Appl. No. 17/193,340, filed Mar. 5, 2021 First Named Inventor: Herriot Tabuteau Assignee: Antecip Bioventures II LLC.
U.S. Appl. No. 17/194,739, filed Mar. 8, 2021 First Named Inventor: Herriot Tabuteau Assignee: Antecip Bioventures II LLC.
U.S. Appl. No. 17/196,338, filed Mar. 9, 2021 First Named Inventor: Herriot Tabuteau Assignee: Antecip Bioventures II LLC.
U.S. Appl. No. 17/197,971, filed Mar. 10, 2021 First Named Inventor: Herriot Tabuteau Assignee: Antecip Bioventures II LLC.
U.S. Appl. No. 17/199,112, filed Mar. 11, 2021 First Named Inventor: Herriot Tabuteau Assignee: Antecip Bioventures II LLC.
U.S. Appl. No. 17/201,820, filed Mar. 15, 2021 First Named Inventor: Herriot Tabuteau Assignee: Antecip Bioventures II LLC.
U.S. Appl. No. 17/207,256, filed Mar. 19, 2021 First Named Inventor: Herriot Tabuteau Assignee: Antecip Bioventures II LLC.
U.S. Appl. No. 17/217,311, filed Mar. 30, 2021 First Named Inventor: Herriot Tabuteau Assignee: Antecip Bioventures II LLC.
U.S. Appl. No. 17/314,647, filed May 7, 2021 First Named Inventor: Herriot Tabuteau Assignee: Antecip Bioventures II LLC.
U.S. Appl. No. 17/316,194, filed May 10, 2021 First Named Inventor: Herriot Tabuteau Assignee: Antecip Bioventures II LLC.
Communication of Notices of Opposition over European Patent No. 3220909 from European Patent Office dated Jun. 25, 2021.
Sansone et al., "Pain, Pain, Go Away: Antidepressants and Pain Management" Psychiatry (Edgemont), 5(12), 16-19, Dec. 2008.
Matsumoto et al., "Involvement of Sigma-1 Receptors in the Antidepressant-like Effects of Dextromethorphan" PLOS One, 9(2), e89985, 1-9, Feb. 2014.
Abdel-Rahman et al., Potent Inhibition of Cytochrome P-450 2D6-mediated Dextromethorphan O-Demethylation by Terbinafine, Drug Metabolism and Disposition, 27(7), 770-775, Jul. 1999.
Bachmann, K., Chapter 12—Drug-drug interactions with an emphasis on drug metabolism and transport, Pharmacology Principles and Practice, Academic Press, 303-325, 2009.
Chyka et al., Dextromethorphan Poisoning: An Evidence-Based Consensus Guideline for Out-of-Hospital Management, Clinical Toxicology, 45(6): 662-677, Sep. 2007.
Desmeules et al., Contribution of Cytochrome P-4502D6 Phenotype to the Neuromodulatory Effects of Dextromethorphan, Journal of Pharmacology and Experimental Therapeutics, 288(2), 607-612, Feb. 1999.

(56) References Cited

OTHER PUBLICATIONS

Dextromethorphan Product Labeling Under the OTC Monograph 21 CFR 341.74, 1 pg., last accessed Nov. 2013.
Droll et al., Comparison of Three CYP2D6 Probe Substrates and Genotype in Ghanaians, Chinese and Caucasians Pharmacogenetics and Genomics, 8(4), 325-333, Aug. 1998.
Drug Interactions between Dextromethorphan/Guaifenesin and Wellbutrin XL®, Drugs.com, last accessed Apr. 11, 2016, 1 pg., available at: http://www.drugs.com/drug-interactions/dextromethorphan-guaifenesin-with-wellbutrin-xl-846-0-440-2469.html.
Fairstein et al., Regional-Dependent Intestinal Permeability and BCS Classification: Elucidation of pH-Related Complexity in Rats Using Pseudoephedrine, The AAPS Journal, 15(2), 589-597, Apr. 2013.
Garnock-Jones, Dextromethorphan/Quinidine: In Pseudobulbar Affect, CNS Drugs, 25(5), 435-45, May 2011.
Gilron et al., A Randomized, Controlled Trial of High-Dose Dextromethorphan in Facial Neuralgias, Neurology, 55 (7), 964-971, Oct. 2000.
Glaxosmithkline, WELLBUTRIN XL® Prescribing Information, 2009, 33 pgs., available at: http://www.accessdata.fda.gov/drugsatfda_docs/label/2009/021515s023s024lbl.pdf.
Glaxosmithkline, ZYBAN® Prescribing Information, Aug. 2011, 28 pgs, available at: http://www.accessdata.fda.gov/drugsatfda_docs/label/2011/020711s026lbl.pdf.
Güzey et al., Change from the CYP2D6 Extensive Metabolizer to the Poor Metabolizer Phenotype During Treatment with Bupropion, Therapeutic Drug Monitoring, 24(3), 436-437, Jun. 2002.
Howard et al., The Efficacy and Toxicity of Bupropion in the Elderly, Jefferson Journal of Psychiatry, 15(1), 34-38, Jan. 2000.
Humanwell Puracap Pharmaceutical (Wuhan), Ltd., Dextromethorphan HBR, Prescribing information, 4 pgs., revised Jan. 2014.
Kelly et al., The Utility of the Combination of Dextromethorphan and Quinidine in the Treatment of Bipolar II and Bipolar NOS, Journal of Affective Disorders, 167, 333-335, Oct. 2014.
Kiptoo et al., Transdermal Delivery of Bupropion and its Active Metabolite, Hydroxybupropion: A Prodrug Strategy as an Alternative Approach, Journal of Pharmaceutical Sciences, 98(2), 583-594, Feb. 2009.
Lauterbach, Dextromethorphan as a Potential Rapid-Acting Antidepressant, Medical Hypotheses, 76(5), 717-719, May 2011.
Lauterbach, An Extension of Hypotheses Regarding Rapid-Acting, Treatment-Refractory, and Conventional Antidepressant Activity of Dextromethorphan and Dextrorphan, Medical Hypotheses, 78(6), 693-702, Jun. 2012.
Lee et al., The DRD2/ANKK1 Gene is Associated with Response to Add-on Dextromethorphan Treatment in Bipolar Disorder, Journal of Affective Disorders, 138(3), 295-300, May 2012.
Mizoguchi et al., Efficacy of a Single Evening Dose of Syrup containing Paracetamol, Dextromethorophan Hydrobromide, Doxylamine Succinate and Ephedrine Sulfate in Subjects with Multiple Common Cold Symptoms, International Journal of Clinical Pharmacology and Therapeutics, 45(4), 230-236, Apr. 2007.
Nakashima et al., Effect of Cinacalcet Hydrochloride, a New Calcimimetic Agent, on the Pharmacokinetics of Dextromethorphan: In Vitro and Clinical Studies, The Journal of Clinical Pharmacology, 47(10), 1311-1319, Oct. 2007.
Nelson et al., High-Dose Oral Dextromethorphan Versus Placebo in Painful Diabetic Neuropathy and Postherpetic Neuralgia, Neurology, 48(5), 1212-1218, May 1997.
Nguyen et al., Involvement of Sigma-1 Receptors in the Antidepressant-like Effects of Dextromethorphan, PLOS One, 9(2), 9 pgs., Feb. 2014.
Olney et al., AVP-923, A Combination of Dextromethorphan Hydrobromide and Quinidine Sulfate for the Treatment of Pseudobulbar Affect and Neuropathic Pain, IDrugs: The Investigational Drugs Journal, 13(4), 254-265, Apr. 2010.
Pioro et al., Dextromethorphan Plus Ultra Low-Dose Quinidine Reduces Pseudobulbar Affect, Annals of Neurology, 68(5), 693-702, Nov. 2010.
Reese et al., An in Vitro Mechanistic Study to Elucidate the Desipramine/Bupropion Clinical Drug-Drug Interaction, Drug Metabolism and Disposition, 36(7), 1198-1201, Jul. 2008.
Rosen, Dextromethorphan/Quinidine Sulfate (ZENVIA™) for Pseudobulbar Affect, Drugs of Today, 44(9), 661-668, Sep. 2008.
Rowley, Regulatory History and Background on Over-the-Counter Dextromethorphan, FDA Drug Safety and Risk Management Advisory Committee Meeting, Presentation, 21 pgs., Sep. 14, 2010.
Sang et al., Dextromethorphan and Memantine in Painful Diabetic Neuropathy and Postherpetic Neuralgia, Anesthesiology, 96(5), 1053-1061, May 2002.
Semenchuk et al., Efficacy of Sustained-Release Bupropion in Neuropathic Pain: An Open-Label Study, The Clinical Journal of Pain, 16(1), 6-11, Mar. 2000.
Semenchuk et al., Double-Blind, Randomized Trial of Bupropion SR for the Treatment of Neuropathic Pain, Neurology, 57(9), 1583-1588, Nov. 2001.
Shah et al., Bupropion for the Treatment of Neuropathic Pain, American Journal of Hospice & Palliative Medicine, 27 (5), 333-336, Aug. 2010.
Shaibani et al., Efficacy and Safety of Dextromethorphan/Quinidine at Two Dosage Levels for Diabetic Neuropathic Pain: A Double-Blind, Placebo-Controlled, Multicenter Study, Pain Medicine, 13(2), 243-254, Feb. 2012.
Silverstone et al., Convulsive Liability of Bupropion Hydrochloride Metabolites in Swiss Albino Mice, Annals of General Psychiatry, 7(1), Article 19, 8 pgs., Oct. 2008.
Smith, Dextromethorphan/Quinidine: A Novel Dextromethorphan Product for the Treatment of Emotional Lability, Expert Opinion on Pharmacotherapy, 7(18), 2581-2598, Dec. 2006.
Spina et al., Clinically Relevant Pharmacokinetic Drug Interactions with Second-Generation Antidepressants: An Update, Clinical Therapeutics, 30(7), 1206-1227, Jul. 2008.
Struthers et al., Mecamylamine, Dihydro-β-Erythroidine, and Dextromethorphan Block Conditioned Responding Evoked by the Conditional Stimulus Effects of Nicotine, Pharmacology, Biochemistry and Behavior, 94(2), 319-328, Dec. 2009.
Thisted et al., Dextromethorphan and Quinidine in Adult Patients with Uncontrolled Painful Diabetic Peripheral Neuropathy: A 29-Day, Multicenter, Open-Label, Dose-Escalation Study, Clinical Therapeutics, 28(10), 1607-1618, Oct. 2006.
U.S. Appl. No. 13/478,023, filed May 22, 2012 First Named Inventor: Herriot Tabuteau Assignee: Antecip Bioventures II LLC.
U.S. Appl. No. 14/550,618, filed Nov. 21, 2014 First Named Inventor: Herriot Tabuteau Assignee: Antecip Bioventures II LLC.
U.S. Appl. No. 14/554,947, filed Nov. 26, 2014 First Named Inventor: Herriot Tabuteau Assignee: Antecip Bioventures II LLC.
U.S. Appl. No. 14/554,988, filed Nov. 26, 2014 First Named Inventor: Herriot Tabuteau Assignee: Antecip Bioventures II LLC.
U.S. Appl. No. 14/555,085, filed Nov. 26, 2014 First Named Inventor: Herriot Tabuteau Assignee: Antecip Bioventures II LLC.
U.S. Appl. No. 14/602,177, filed Jan. 21, 2015 First Named Inventor: Herriot Tabuteau Assignee: Antecip Bioventures II LLC.
U.S. Appl. No. 14/604,397, filed Jan. 23, 2015 First Named Inventor: Herriot Tabuteau Assignee: Antecip Bioventures II LLC.
U.S. Appl. No. 14/617,624, filed Feb. 9, 2015 First Named Inventor: Herriot Tabuteau Assignee: Antecip Bioventures II LLC.
U.S. Appl. No. 14/628,062, filed Feb. 20, 2015 First Named Inventor: Herriot Tabuteau Assignee: Antecip Bioventures II LLC.
U.S. Appl. No. 14/863,284, filed Sep. 23, 2015 First Named Inventor: Herriot Tabuteau Assignee: Antecip Bioventures II LLC.
U.S. Appl. No. 14/878,998, filed Oct. 8, 2015 First Named Inventor: Herriot Tabuteau Assignee: Antecip Bioventures II LLC.
U.S. Appl. No. 14/879,002, filed Oct. 8, 2015 First Named Inventor: Herriot Tabuteau Assignee: Antecip Bioventures II LLC.
U.S. Appl. No. 14/978,976, filed Dec. 22, 2015 First Named Inventor: Herriot Tabuteau Assignee: Antecip Bioventures II LLC.
U.S. Appl. No. 14/997,316, filed Jan. 15, 2016 First Named Inventor: Herriot Tabuteau Assignee: Antecip Bioventures II LLC.
U.S. Appl. No. 15/057,983, filed Mar. 1, 2016 First Named Inventor: Herriot Tabuteau Assignee: Antecip Bioventures II LLC.
U.S. Appl. No. 15/130,807, filed Apr. 15, 2016 First Named Inventor: Herriot Tabuteau Assignee: Antecip Bioventures II LLC.

(56) References Cited

OTHER PUBLICATIONS

U.S. Appl. No. 15/164,746, filed May 25, 2016 First Named Inventor: Herriot Tabuteau Assignee: Antecip Bioventures II LLC.
U.S. Appl. No. 15/164,767, filed May 25, 2016 First Named Inventor: Herriot Tabuteau Assignee: Antecip Bioventures II LLC.
U.S. Appl. No. 15/206,057, filed Jul. 8, 2016 First Named Inventor: Herriot Tabuteau Assignee: Antecip Bioventures II LLC.
U.S. Appl. No. 15/182,253, filed Jun. 14, 2016 First Named Inventor: Herriot Tabuteau Assignee: Antecip Bioventures II LLC.
Wadhwa et al., Large-Dose Oral Dextromethorphan as an Adjunct to Patient-Controlled Analgesia with Morphine after Knee Surgery, Anesthesia & Analgesia, 92(2), 448-454, Feb. 2001.
Walker et al., An Open Label Trial of Dextromethorphan in Huntington's Disease, Clinical Neuropharmacology, 12 (4), 322-330, Aug. 1989.
Weinbroum et al., The Role of Dextromethorphan in Pain Control, Canadian Journal of Anesthesia, 47(6), 585-596, Jun. 2000.
Zhu et al., CYP2B6 and Bupropion's Smoking-Cessation Pharmacology: The Role of Hydroxybupropion, Clinical Pharmacology & Therapeutics, 92(6), 771-777, Dec. 2012.
U.S. Appl. No. 15/213,283, filed Jul. 18, 2016 First Named Inventor: Herriot Tabuteau Assignee: Antecip Bioventures II LLC.
U.S. Appl. No. 15/216,545, filed Jul. 21, 2016 First Named Inventor: Herriot Tabuteau Assignee: Antecip Bioventures II LLC.
U.S. Appl. No. 15/224,233, filed Jul. 29, 2016 First Named Inventor: Herriot Tabuteau Assignee: Antecip Bioventures II LLC.
Jefferson, J. W., et al. (2005) "Bupropion for Major Depressive Disorder: Pharmacokinetic and Formulation Considerations," Clinical Therapeutics : vol. 27(11), pp. 1685-1695.
U.S. Appl. No. 15/236,290, filed Aug. 12, 2016 First Named Inventor: Herriot Tabuteau Assignee: Antecip Bioventures II LLC.
U.S. Appl. No. 15/238,182, filed Aug. 16, 2016 First Named Inventor: Herriot Tabuteau Assignee: Antecip Bioventures II LLC.
U.S. Appl. No. 15/263,138, filed Sep. 12, 2016 First Named Inventor: Herriot Tabuteau Assignee: Antecip Bioventures II LLC.
U.S. Appl. No. 15/275,177, filed Sep. 23, 2016 First named Inventor: Herriot Tabuteau Assignee: Antecip Bioventures II LLC.
U.S. Appl. No. 15/280,938, filed Sep. 29, 2016 First named Inventor: Herriot Tabuteau Assignee: Antecip Bioventures II LLC.
"Avanir & Concert Announce Exclusive License Agreement," http://drug-dev.com/Main/Current-News/362012-573, aspx, Mar. 6, 2012, publication.
Wellbutrin XL (bupropion hydrochloride extended-release) tablets for oral use, Dec. 2014.
Devane, Hum. Psychopharmacol. Clin. Exp. 13:5, 329-336,1998.
Dwoskin et al., "Review of the Pharmacology and Clinical Profile of Bupropion, an Antidepressant and Tobacco Use Cessation Agent," CNS Drug Reviews, v12, No. 3-4, pp. 178-207, 2006.
Extended European Search Report for EP14859589 (corresponding to PCT/US2014064184), dated Mar. 8, 2017.
US Patent Application No. PCT/US2017/024140 Filed: Mar. 24, 2017 First named Inventor: Herriot Tabuteau Assignee: Antecip Bioventures II LLC.
U.S. Appl. No. 15/599,163, filed May 18, 2017 First named Inventor: Herriot Tabuteau Assignee: Antecip Bioventures II LLC.
U.S. Appl. No. 15/621,882, filed Jun. 13, 2017 First named Inventor: Herriot Tabuteau Assignee: Antecip Bioventures II LLC.
U.S. Appl. No. 15/645,939, filed Jul. 10, 2017 First named Inventor: Herriot Tabuteau Assignee: Antecip Bioventures II LLC.
U.S. Appl. No. 15/647,069, filed Jul. 11, 2017 First named Inventor: Herriot Tabuteau Assignee: Antecip Bioventures II LLC.
U.S. Appl. No. 15/647,852, filed Jul. 12, 2017 First named Inventor: Herriot Tabuteau Assignee: Antecip Bioventures II LLC.
U.S. Appl. No. 15/688,660, filed Aug. 28, 2017 First named Inventor: Herriot Tabuteau Assignee: Antecip Bioventures II LLC.
U.S. Appl. No. 15/691,532, filed Aug. 30, 2017 First named Inventor: Herriot Tabuteau Assignee: Antecip Bioventures II LLC.
U.S. Appl. No. 15/691,549, filed Aug. 30, 2017 First named Inventor: Herriot Tabuteau Assignee: Antecip Bioventures II LLC.
U.S. Appl. No. 15/695,995, filed Sep. 5, 2017 First named Inventor: Herriot Tabuteau Assignee: Antecip Bioventures II LLC.
U.S. Appl. No. 15/821,563, filed Nov. 22, 2017 First named Inventor: Herriot Tabuteau Assignee: Antecip Bioventures II LLC.
U.S. Appl. No. 15/842,599, filed Dec. 14, 2017 First named Inventor: Herriot Tabuteau Assignee: Antecip Bioventures II LLC.
U.S. Appl. No. 15/856,853, filed Dec. 28, 2017 First named Inventor: Herriot Tabuteau Assignee: Antecip Bioventures II LLC.
U.S. Appl. No. 15/933,075, filed Mar. 22, 2018 First named Inventor: Herriot Tabuteau Assignee: Antecip Bioventures II LLC.
U.S. Appl. No. 15/977,276, filed May 11, 2018 First named Inventor: Herriot Tabuteau Assignee: Antecip Bioventures II LLC.
Coles et al., "Stereoselective Metabolism of Bupropion by Cytochrome P4502B6 (CYP2B6) and Human Liver Microsomes", Pharmaceutical Research, vol. 25, No. 6, 1405-1411, Jun. 2008.
Coles et al., "Stereoselective Analysis of Bupropion and Hydroxybupropion in Human Plasma and Urine by LC/MS/MS", Journal of Chromatography B, vol. 857, No. 1, 67-75, Sep. 2007.
Joy et al., "Use of Enantiomeric Bupropion and Hydroxybupropion to Assess CYP2B6 Activity in Glomerular Kidney Diseases", Journal of Clinical Pharmacology, 50, 714-720, 2010.
Sager et al., "In Vitro to In Vivo Extrapolation of the Complex Drug-Drug Interaction of Bupropion and Its Metabolites with CYP2D6; Simultaneous Reversible Inhibition and CYP2D6 Downregulation", Biochem. Pharmacol., 123, 85-96, Jan. 2017.
Wellbutrin SR® "Information for the Patient", Glaxo Wellcome Inc. North Carolina USA, Mar. 2001.
Siu et al., "Dextromethorphan: A Review of N-methyl-D-aspartate Receptor Antagonist in the Management of Pain", DNS Drug Reviews, 13(1), 96-106, 2007.
Shah et al., "Bupropion for the Treatment of Neuropathic Pain", American Journal of Hospice & Palliative Medicine, 27 (5), 333-336, 2010.
U.S. Appl. No. 17/373,299, filed Jul. 12, 2021 First Named Inventor: Herriot Tabuteau Assignee: Antecip Bioventures II LLC.
U.S. Appl. No. 17/380,751, filed Jul. 20, 2021 First Named Inventor: Herriot Tabuteau Assignee: Antecip Bioventures II LLC.
U.S. Appl. No. 17/395,222, filed Aug. 5, 2021 First Named Inventor: Herriot Tabuteau Assignee: Antecip Bioventures II LLC.
U.S. Appl. No. 17/405,429, filed Aug. 18, 2021 First Named Inventor: Herriot Tabuteau Assignee: Antecip Bioventures II LLC.
International Preliminary Report on Patentability, PCT/US2020/012612, dated Jul. 22, 2021.
U.S. Appl. No. 17/468,149, filed Sep. 7, 2021 First Named Inventor: Herriot Tabuteau Assignee: Antecip Bioventures II LLC.
U.S. Appl. No. 17/470,831, filed Sep. 9, 2021 First Named Inventor: Herriot Tabuteau Assignee: Antecip Bioventures II LLC.
U.S. Appl. No. 17/471,983, filed Sep. 10, 2021 First Named Inventor: Herriot Tabuteau Assignee: Antecip Bioventures II LLC.
U.S. Appl. No. 17/473,860, filed Sep. 13, 2021 First Named Inventor: Herriot Tabuteau Assignee: Antecip Bioventures II LLC.
U.S. Appl. No. 17/482,241, filed Sep. 22, 2021 First Named Inventor: Herriot Tabuteau Assignee: Antecip Bioventures II LLC.
U.S. Appl. No. 17/498,507, filed Oct. 11, 2021 First Named Inventor: Herriot Tabuteau Assignee: Antecip Bioventures II LLC.
U.S. Appl. No. 17/525,339, filed Nov. 12, 2021 First Named Inventor: Herriot Tabuteau Assignee: Antecip Bioventures II LLC.
U.S. Appl. No. 17/526,676, filed Nov. 15, 2021 First Named Inventor: Herriot Tabuteau Assignee: Antecip Bioventures II LLC.
U.S. Appl. No. 17/541,461, filed Dec. 3, 2021 First Named Inventor: Herriot Tabuteau Assignee: Antecip Bioventures II LLC.
U.S. Appl. No. 17/547,050, filed Dec. 9, 2021 First Named Inventor: Herriot Tabuteau Assignee: Antecip Bioventures II LLC.
U.S. Appl. No. 17/571,110, filed Jan. 7, 2022 First Named Inventor: Herriot Tabuteau Assignee: Antecip Bioventures II LLC.
U.S. Appl. No. 17/574,378, filed Jan. 12, 2022 First Named Inventor: Herriot Tabuteau Assignee: Antecip Bioventures II LLC.
U.S. Appl. No. 17/581,292, filed Jan. 21, 2022 First Named Inventor: Herriot Tabuteau Assignee: Antecip Bioventures II LLC.
U.S. Appl. No. 17/693,711, filed Mar. 14, 2022 First Named Inventor: Herriot Tabuteau Assignee: Antecip Bioventures II LLC.
U.S. Appl. No. 17/705,930, filed Mar. 28, 2022 First Named Inventor: Herriot Tabuteau Assignee: Antecip Bioventures II LLC.

(56) References Cited

OTHER PUBLICATIONS

U.S. Appl. No. 17/707,221, filed Mar. 29, 2022 First Named Inventor: Herriot Tabuteau Assignee: Antecip Bioventures II LLC.
U.S. Appl. No. 17/657,832, filed Apr. 4, 2022 First Named Inventor: Herriot Tabuteau Assignee: Antecip Bioventures II LLC.
U.S. Appl. No. 17/712,970, filed Apr. 4, 2022 First Named Inventor: Herriot Tabuteau Assignee: Antecip Bioventures II LLC.
U.S. Appl. No. 17/716,796, filed Apr. 8, 2022 First Named Inventor: Herriot Tabuteau Assignee: Antecip Bioventures II LLC.
U.S. Appl. No. 17/717,516, filed Apr. 11, 2022 First Named Inventor: Herriot Tabuteau Assignee: Antecip Bioventures II LLC.
U.S. Appl. No. 17/721,827, filed Apr. 15, 2022 First Named Inventor: Herriot Tabuteau Assignee: Antecip Bioventures II LLC.
Siffert, Letters to the Editor, Dextromethorphan/Quinidine for Agitation in Alzheimer's Disease, Neurology Today, Nov. 2015 (/neurotodayonline/pages/default.aspx).
U.S. Appl. No. 17/730,814, filed Apr. 27, 2022 First Named Inventor: Herriot Tabuteau Assignee: Antecip Bioventures II LLC.
U.S. Appl. No. 17/735,470, filed May 3, 2022 First Named Inventor: Herriot Tabuteau Assignee: Antecip Bioventures II LLC.
U.S. Appl. No. 17/748,475, filed May 19, 2022 First Named Inventor: Herriot Tabuteau Assignee: Antecip Bioventures II LLC.
U.S. Appl. No. 17/836,560, filed Jun. 9, 2022 First Named Inventor: Herriot Tabuteau Assignee: Antecip Bioventures II LLC.
U.S. Appl. No. 17/841,274, filed Jun. 15, 2022 First Named Inventor: Herriot Tabuteau Assignee: Antecip Bioventures II LLC.
Wood et al., OTC Dextromethorphan-Induced Serotonin Syndrome, U.S. Pharmacist, Apr. 2010. (https://www.uspharmacist.com/article/otc-dextromethorphan-induced-serotonin-syndrome).
Hurt et al., A Comparison of Sustained-Release Bupropion and Placebo for Smoking Cessation, New England Journal of Medicine, 337(17), 1195-202, Oct. 1997.
International Preliminary Report on Patentability with Written Opinion, PCT/US2021/024718, dated Oct. 13, 2022.
Anderson, A. et al., Efficacy and Safety of AXS-05, an Oral NMDA Receptor Antagonist with Multimodal Activity, in Major Depressive Disorder: Results of a Phase 2, Double-Blind, Active-Controlled Trial, W43 ASCP Annual Meeting, May 2019 [retrieved on Nov. 1, 2022], (URL:https://d3dyybxyjb4kyh.cloudfront.net/pdfs/Axsome-AXS-05-Poster-Presentation-ASCP2019.pdf).
O'Gorman, C. et al., AXS-05: A Mechanistically Novel Oral Therapeutic in Development for Neuropsychiatric Disorders, P7-141 APA Annual Meeting, May 2019 [retrieved on Nov. 1, 2022], (URL:https://d3dyybxyjb4kyh.cloudfrontnet/pdfs/Axsome-AXS-05-Poster-APA-2019-1.pdf).
O'Gorman, C. et al., AXS-05 (Dextromethorphan/Bupropion): An Innovative Treatment in Clinical Development for Agitation Associated with Alzheimer's Disease, P2-033 AAIC Conference, Jul. 2018 [retrieved on Nov. 1, 2022], URL:https://d3dyybxyjb4kyh.cloudfront.net/pdfs/Axsome-AXS-05-Poster-AAIC-2018-1-1.pdf).
Stahl, S.M., Dextromethorphan/Bupropion: A Novel Oral NMDA (N-methyl-d-aspartate) Receptor Antagonist with Multimodal Activity, CNS Spectrums, vol. 24, Issue 5, pp. 461-466, published online Sep. 30, 2019 [retrieved on Nov. 1, 2022], (D01:10.1017/S1092852919001470).
AXS Pipeline: About AXS-05 [online], AXSOME, retrieved on Nov. 1, 2022 from https://www.axsome.com/axs-portfolio/pipeline/about-axs-05.
International Search Report, PCT/US2021/024718.
Written Opinion of the International Searching Authority for PCT/US2014/071519 (corresponding to WO2015095713) dated Feb. 10, 2015.
U.S. Appl. No. 16/107,472, filed Aug. 21, 2018 First Named Inventor: Herriot Tabuteau Assignee: Antecip Bioventures II LLC.
U.S. Appl. No. 16/116,393, filed Aug. 29, 2018 First Named Inventor: Herriot Tabuteau Assignee: Antecip Bioventures II LLC.
U.S. Appl. No. 16/119,852, filed Aug. 31, 2018 First Named Inventor: Herriot Tabuteau Assignee: Antecip Bioventures II LLC.
U.S. Appl. No. 16/127,832, filed Sep. 11, 2018 First Named Inventor: Herriot Tabuteau Assignee: Antecip Bioventures II LLC.
U.S. Appl. No. 16/129,531, filed Sep. 12, 2018 First Named Inventor: Herriot Tabuteau Assignee: Antecip Bioventures II LLC.
U.S. Appl. No. 16/130,898, filed Sep. 13, 2018 First Named Inventor: Herriot Tabuteau Assignee: Antecip Bioventures II LLC.
U.S. Appl. No. 16/133,553, filed Sep. 17, 2018 First Named Inventor: Herriot Tabuteau Assignee: Antecip Bioventures II LLC.
U.S. Appl. No. 16/246,347, filed Jan. 11, 2019 First Named Inventor: Herriot Tabuteau Assignee: Antecip Bioventures II LLC.
U.S. Appl. No. 16/290,653, filed Mar. 1, 2019 First Named Inventor: Herriot Tabuteau Assignee: Antecip Bioventures II LLC.
U.S. Appl. No. 16/359,958, filed Mar. 20, 2019 First Named Inventor: Herriot Tabuteau Assignee: Antecip Bioventures II LLC.
U.S. Appl. No. 16/359,996, filed Mar. 20, 2019 First Named Inventor: Herriot Tabuteau Assignee: Antecip Bioventures II LLC.
U.S. Appl. No. 16/364,005, filed Mar. 25, 2019 First Named Inventor: Herriot Tabuteau Assignee: Antecip Bioventures II LLC.
U.S. Appl. No. 16/364,463, filed Mar. 26, 2019 First Named Inventor: Herriot Tabuteau Assignee: Axsome Therapeutics, Inc.
U.S. Appl. No. 16/579,305, filed Sep. 23, 2019 First Named Inventor: Herriot Tabuteau Assignee: Axsome Therapeutics, Inc.
U.S. Appl. No. 16/588,399, filed Sep. 30, 2019 First Named Inventor: Herriot Tabuteau Assignee: Antecip Bioventures II LLC.
U.S. Appl. No. 16/681,317, filed Nov. 12, 2019 First Named Inventor: Herriot Tabuteau Assignee: Antecip Bioventures II LLC.
Murrough et al., Dextromethorphan/quinidine pharmacotherapy in patients with treatment resistant depression: a proof of concept clinical trial, Journal of affective disorders, 218, 271-283, Aug. 2017.
U.S. Appl. No. 16/736,752, filed Jan. 7, 2020 First Named Inventor: Herriot Tabuteau Assignee: Antecip Bioventures II LLC.
U.S. Appl. No. 16/745,105, filed Jan. 16, 2020 First Named Inventor: Herriot Tabuteau Assignee: Antecip Bioventures II LLC.
Drugs.com, Bupropion Hydrochloride, Feb. 5, 2018.
U.S. Appl. No. 16/817,119, filed Mar. 12, 2020 First Named Inventor: Herriot Tabuteau Assignee: Antecip Bioventures II LLC.
U.S. Appl. No. 16/821,330, filed Mar. 17, 2020 First Named Inventor: Herriot Tabuteau Assignee: Antecip Bioventures II LLC.
U.S. Appl. No. 16/821,462, filed Mar. 17, 2020 First Named Inventor: Herriot Tabuteau Assignee: Antecip Bioventures II LLC.
U.S. Appl. No. 16/822,564, filed Mar. 18, 2020 First Named Inventor: Herriot Tabuteau Assignee: Antecip Bioventures II LLC.
U.S. Appl. No. 16/822,697, filed Mar. 18, 2020 First Named Inventor: Herriot Tabuteau Assignee: Antecip Bioventures II LLC.
U.S. Appl. No. 16/823,724, filed Mar. 19, 2020 First Named Inventor: Herriot Tabuteau Assignee: Antecip Bioventures II LLC.
U.S. Appl. No. 16/823,807, filed Mar. 19, 2020 First Named Inventor: Herriot Tabuteau Assignee: Antecip Bioventures II LLC.
U.S. Appl. No. 16/825,195, filed Mar. 20, 2020 First Named Inventor: Herriot Tabuteau Assignee: Antecip Bioventures II LLC.
U.S. Appl. No. 16/825,228, filed Mar. 20, 2020 First Named Inventor: Herriot Tabuteau Assignee: Antecip Bioventures II LLC.
U.S. Appl. No. 16/826,580, filed Mar. 23, 2020 First Named Inventor: Herriot Tabuteau Assignee: Antecip Bioventures II LLC.
U.S. Appl. No. 16/826,598, filed Mar. 23, 2020 First Named Inventor: Herriot Tabuteau Assignee: Antecip Bioventures II LLC.
U.S. Appl. No. 16/828,237, filed Mar. 24, 2020 First Named Inventor: Herriot Tabuteau Assignee: Antecip Bioventures II LLC.
U.S. Appl. No. 16/838,829, filed Apr. 2, 2020 First Named Inventor: Herriot Tabuteau Assignee: Antecip Bioventures II LLC.
*Avanir Pharmaceuticals* v. *Actavis South Atlantic*, Cite as 36 F.Supp.3d 475 (D.Del. 2014), accessed on Apr. 16, 2020.
U.S. Appl. No. 16/852,939, filed Apr. 20, 2020 First Named Inventor: Herriot Tabuteau Assignee: Antecip Bioventures II LLC.
U.S. Appl. No. 16/853,062, filed Apr. 20, 2020 First Named Inventor: Herriot Tabuteau Assignee: Antecip Bioventures II LLC.
International Search Report and Written Opinion of the International Searching Authority for PCT/US2020/012612, dated Apr. 30, 2020.
Lauterbach, Treatment Resistant Depression with Loss of Antidepressant Response: Rapid—Acting Antidepressant Action of Dextromethorphan, a Possible Treatment Bridging Molecule, Psychopharmacology Bulletin, 16(2), 53-57, Aug. 2016.

(56) References Cited

OTHER PUBLICATIONS

Koshino et al., The efficacy and safety of bupropion sustained-release formulation for the treatment of major depressive disorder: a multi-center, randomized, double-blind, placebo-controlled study in Asian patients, Neuropsychiatric Disease and Treatment, 9, 1273-1280, Aug. 2013.
Sheng et al., Sustained-Release Bupropion for Smoking Cessation in a Chinese Sample: A Double-Blind,Placebo-Controlled, Randomized Trial, Nicotine &Tobacco Research, 15(2), 320-325, Feb. 2013.
Leelahanaj, Developing Thai Economic Model to Study Cost-Effectiveness of Switching to Bupropion Compared to Combination with Bupropion after the Failure of an SSRI for Major Depressive Disorder, J Med Assoc Thai, 93 (Suppl 6), S35-S42, 2010.
Nofziger et al., Evaluation of dextromethorphan with select antidepressant therapy for the treatment of depression in the acute care psychiatric setting, Mental Health Clinician, 9(2), 76-81, Mar. 2019.
SPRAVATO™ (esketamine) Highlights of Prescribing Information, Mar. 2019.
Gideons et al., Mechanisms underlying differential effectiveness of memantine and ketamine in rapid antidepressant responses, Proceedings of the National Academy of Sciences, 111(23), 8649-8654, Jun. 2014.
Muhonen et al., Double-Blind, Randomized Comparison of Memantine and Escitalopram for the Treatment of Major Depressive Disorder Comorbid with Alcohol Dependence, The Journal of Clinical Psychiatry, 69(3), 392-399, Mar. 2008.
"Rapastinel Fails to Outperform Placebo in Phase 3 Studies", Mar. 2019, downloaded from https://www.psychcongress.com/article/rapastinel-fails-outperform-placebo-phase-3-studies, on May 28, 2020.
Rogoz et al., Amantadine as an additive treatment in patients suffering from drug-resistant unipolar depression, Pharmacological Reports, 59(6), 778-784, Nov. 2007.
Smith et al., Antidepressant Augmentation Using the NMDA-Antagonist Memantine: a Randomized, Double-Blind, Placebo-Controlled Trial, The Journal of Clinical Psychiatry, 74(10), 966-973, Oct. 2013.
Wright Jr. et al., Comparative Effects of Dextromethorphan and Dextrorphan on Nicotine Discrimination in Rats, Pharmacology Biochemistry and Behavior, 85(3), 507-513, Nov. 2006.
U.S. Appl. No. 17/929,147, filed Sep. 1, 2022 First Named Inventor: Herriot Tabuteau Assignee: Antecip Bioventures II LLC.
U.S. Appl. No. 17/930,829, filed Sep. 9, 2022 First Named Inventor: Herriot Tabuteau Assignee: Antecip Bioventures II LLC.
U.S. Appl. No. 17/471,895, filed Sep. 10, 2021 First Named Inventor: Herriot Tabuteau Assignee: Antecip Bioventures II LLC.
U.S. Appl. No. 18/056,804, filed Nov. 18, 2022 First Named Inventor: Herriot Tabuteau Assignee: Antecip Bioventures II LLC.
U.S. Appl. No. 18/056,848, filed Nov. 18, 2022 First Named Inventor: Herriot Tabuteau Assignee: Antecip Bioventures II LLC.
U.S. Appl. No. 18/061,091, filed Dec. 2, 2022 First Named Inventor: Herriot Tabuteau Assignee: Antecip Bioventures II LLC.
U.S. Appl. No. 18/062,236, filed Dec. 6, 2022 First Named Inventor: Herriot Tabuteau Assignee: Antecip Bioventures II LLC.
U.S. Appl. No. 18/062,273, filed Dec. 6, 2022 First Named Inventor: Herriot Tabuteau Assignee: Antecip Bioventures II LLC.
U.S. Appl. No. 18/063,261, filed Dec. 8, 2022 First Named Inventor: Herriot Tabuteau Assignee: Antecip Bioventures II LLC.
U.S. Appl. No. 18/066,739, filed Dec. 15, 2022 First Named Inventor: Herriot Tabuteau Assignee: Antecip Bioventures II LLC.
U.S. Appl. No. 18/156,825, filed Jan. 19, 2023 First Named Inventor: Herriot Tabuteau Assignee: Antecip Bioventures II LLC.
U.S. Appl. No. 18/157,266, filed Jan. 20, 2023 First Named Inventor: Herriot Tabuteau Assignee: Antecip Bioventures II LLC.
U.S. Appl. No. 18/157,393, filed Jan. 20, 2023 First Named Inventor: Herriot Tabuteau Assignee: Antecip Bioventures II LLC.
U.S. Appl. No. 18/158,268, filed Jan. 23, 2023 First Named Inventor: Herriot Tabuteau Assignee: Antecip Bioventures II LLC.
U.S. Appl. No. 18/169,571, filed Feb. 15, 2023 First Named Inventor: Herriot Tabuteau Assignee: Antecip Bioventures II LLC.
U.S. Appl. No. 18/170,120, filed Feb. 16, 2023 First Named Inventor: Herriot Tabuteau Assignee: Antecip Bioventures II LLC.
U.S. Appl. No. 18/170,151, filed Feb. 16, 2023 First Named Inventor: Herriot Tabuteau Assignee: Antecip Bioventures II LLC.
U.S. Appl. No. 18/172,555, filed Feb. 22, 2023 First Named Inventor: Herriot Tabuteau Assignee: Antecip Bioventures II LLC.
U.S. Appl. No. 18/172,617, filed Feb. 22, 2023 First Named Inventor: Herriot Tabuteau Assignee: Antecip Bioventures II LLC.
U.S. Appl. No. 18/173,291, filed Feb. 23, 2023 First Named Inventor: Herriot Tabuteau Assignee: Antecip Bioventures II LLC.
U.S. Appl. No. 18/173,372, filed Feb. 23, 2023 First Named Inventor: Herriot Tabuteau Assignee: Antecip Bioventures II LLC.
U.S. Appl. No. 18/174,123, filed Feb. 24, 2023 First Named Inventor: Herriot Tabuteau Assignee: Antecip Bioventures II LLC.
U.S. Appl. No. 18/174,278, filed Feb. 24, 2023 First Named Inventor: Herriot Tabuteau Assignee: Antecip Bioventures II LLC.
U.S. Appl. No. 18/175,862, filed Feb. 28, 2023 First Named Inventor: Herriot Tabuteau Assignee: Antecip Bioventures II LLC.
U.S. Appl. No. 18/175,865, filed Feb. 28, 2023 First Named Inventor: Herriot Tabuteau Assignee: Antecip Bioventures II LLC.
Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.
Auvelity (dextromethorphan hydrobromide and bupropion hydrochloride), Highlights of Prescribing Information and Medication Guide, issued Dec. 2022.

\* cited by examiner

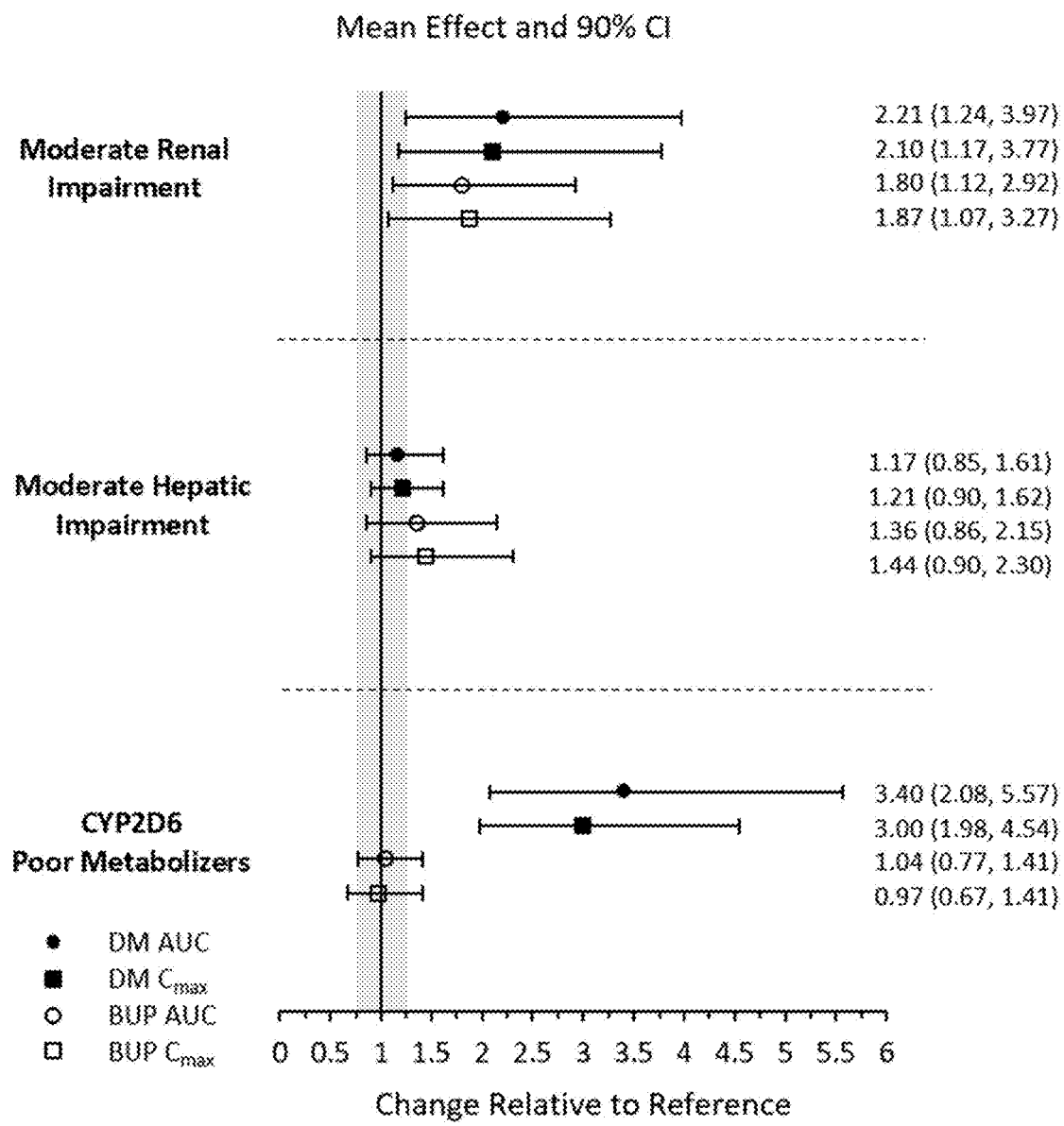
Effects of Renal Impairment, Hepatic Impairment, and CYP2D6 Poor Metabolizer Status on Dextromethorphan/Bupropion PK

TREATMENT OF DEPRESSION IN CERTAIN PATIENT POPULATIONS

CROSS-REFERENCE TO RELATED APPLICATIONS

This application claims priority to U.S. Provisional Patent Application No. 63/359,143, filed Jul. 7, 2022, U.S. Provisional Patent Application No. 63/370,592, filed Aug. 5, 2022, U.S. Provisional Patent Application No. 63/396,182, filed Aug. 8, 2022, U.S. Provisional Patent Application No. 63/373,040, filed Aug. 19, 2022, and U.S. Provisional Patent Application No. 63/401,541, filed Aug. 26, 2022, all of which are incorporated by reference herein in their entireties.

SUMMARY

This disclosure relates to administration of a combination of: 1) about 100-110 mg, about 104-106 mg, or about 105 mg of bupropion hydrochloride, or a molar equivalent amount of a free base form or another salt form of dextromethorphan; and 2) about 40-50 mg, about 44-46 mg, or about 45 mg of dextromethorphan hydrobromide, or a molar equivalent amount of a free base form or another salt form of dextromethorphan in certain patient populations.

Some embodiments include a method of treating major depressive disorder in a patient having moderate renal impairment, comprising administering a daily dose of: (i) about 105 mg of bupropion hydrochloride and (ii) about 45 mg of dextromethorphan hydrobromide to a human patient who has moderate renal impairment and is experiencing major depressive disorder.

Some embodiments include a method of treating major depressive disorder in a patient receiving a concomitant strong CYP2D6 inhibitor, comprising administering a daily dose of: (i) about 105 mg of bupropion hydrochloride and (ii) about 45 mg of dextromethorphan hydrobromide to a human patient who has major depressive disorder and is receiving concomitant treatment with a strong CYP2D6 inhibitor.

Some embodiments include a method of treating major depressive disorder in a patient who is a known CYP2D6 poor metabolizer, comprising administering a daily dose of: (i) about 105 mg of bupropion hydrochloride and (ii) about 45 mg of dextromethorphan hydrobromide to a human patient who is experiencing major depressive disorder and is known to be a CYP2D6 poor metabolizer.

Some embodiments include a method of using an N-methyl D-aspartate (NMDA) receptor antagonist to treat major depressive disorder, comprising administering, no more than twice daily, a combination of 105 mg of bupropion hydrochloride and 45 mg of dextromethorphan hydrobromide to a human patient who is experiencing major depressive disorder, wherein the dextromethorphan acts as an uncompetitive antagonist of the NMDA receptor and a sigma-1 receptor agonist, and the human patient does not experience dissociation.

Some embodiments include a method of treating major depressive disorder in a human patient at risk of QT prolongation, comprising administering, no more than twice daily, a combination of 105 mg of bupropion hydrochloride and 45 mg of dextromethorphan hydrobromide to a human patient who is experiencing major depressive disorder and is at risk of QT prolongation and torsades de pointer, wherein electrocardiographic evaluation of QT interval is not conducted on the human patient.

BRIEF DESCRIPTION OF THE DRAWINGS

FIG. 1 depicts the effects of renal impairment, hepatic impairment, and CYP2D6 poor metabolizer status on the pharmacokinetics of a tablet containing 45 mg of dextromethorphan hydrobromide and 105 mg of bupropion hydrochloride.

DETAILED DESCRIPTION

As mentioned above, this disclosure relates to administration of a combination of: 1) about 100-110 mg, about 104-106 mg, or about 105 mg of bupropion hydrochloride, or a molar equivalent amount of a free base form or another salt form of dextromethorphan; and 2) about 40-50 mg, about 44-46 mg, or about 45 mg of dextromethorphan hydrobromide, or a molar equivalent amount of a free base form or another salt form of dextromethorphan. This combination is referred to for convenience herein as the "subject combination." In every instance where the subject combination is referred to herein, the combination of 105 mg of bupropion hydrochloride and 45 mg of dextromethorphan hydrobromide is specifically contemplated.

Dextromethorphan hydrobromide is an uncompetitive NMDA receptor antagonist and A sigma-1 receptor agonist.

The chemical name of dextromethorphan hydrobromide is morphinan, 3-methoxy-17-methyl-, (9a, 13a, 14a), hydrobromide monohydrate. Dextromethorphan hydrobromide has the empirical formula $C_{18}H_{25}NO \cdot HBr \cdot H_2O$ and a molecular weight of 370.33. The structural formula is:

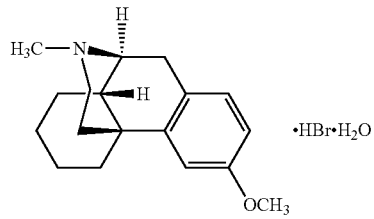

Dextromethorphan hydrobromide powder is white or almost white, crystalline, and sparingly soluble in water.

Bupropion hydrochloride is an aminoketone and CYP450 2D6 inhibitor.

The chemical name of bupropion hydrochloride is: (±)-1-(3-chlorophenyl)-2-[(1,1-dimethylethyl)amino]-1-propanone hydrochloride. Bupropion hydrochloride has the empirical formula $C_{13}H_{18}ClNO \cdot HCl$ and a molecular weight of 276.2. The structural formula is:

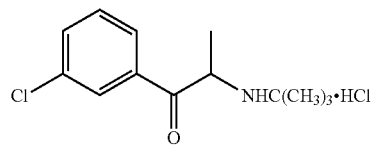

Bupropion hydrochloride powder is white and highly soluble in water.

The subject combination may be contained in an oral dosage form, including a tablet, such as an extended-release tablet. In some embodiments, the subject combination is contained in a dosage form for oral administration and is available as round bilayer tablets.

In some embodiments, each tablet containing the subject combination contains 45 mg of dextromethorphan hydrobromide in an immediate-release formulation. In some embodiments, each tablet of the subject combination contains 105 mg of bupropion hydrochloride in an extended-release formulation. In some embodiments, each tablet of the subject combination contains 45 mg of dextromethorphan hydrobromide in an immediate-release formulation and 105 mg of bupropion hydrochloride in an extended-release formulation.

In some embodiments, a tablet containing the subject combination contains 1-cysteine hydrochloride monohydrate. In some embodiments, a tablet containing the subject combination contains carbomer homopolymer. In some embodiments, a tablet containing the subject combination contains microcrystalline cellulose. In some embodiments, a tablet containing the subject combination contains colloidal silicon dioxide. In some embodiments, a tablet containing the subject combination contains crospovidone. In some embodiments, a tablet containing the subject combination contains stearic acid. In some embodiments, a tablet containing the subject combination contains magnesium stearate.

In some embodiments, a tablet containing the subject combination contains the following inactive ingredients: 1-cysteine hydrochloride monohydrate, carbomer homopolymer, microcrystalline cellulose, colloidal silicon dioxide, crospovidone, stearic acid, and magnesium stearate.

In some embodiments, the starting dosage of the subject combination is 45 mg of dextromethorphan hydrobromide and 105 mg of bupropion hydrochloride in one tablet that is administered once daily in the morning. In some embodiments, after 3 days, the dosage is increased to one tablet (or one dosage form containing 45 mg of dextromethorphan hydrobromide and 105 mg of bupropion hydrochloride) twice daily, e.g., given at least 8 hours apart. In some embodiments, no more than two doses containing 45 mg of dextromethorphan hydrobromide and 105 mg of bupropion hydrochloride are administered in the same day.

The subject combination may be administered orally with or without food. In some embodiments, the tablets are swallowed whole, and not crushed, divided, or chewed.

Patients having renal impairment may require special dosing. In some embodiments, the recommended dosage of the subject combination for patients with moderate renal impairment (estimated glomerular filtration rate (eGFR) or glomerular filtration rate (GFR) of 30 to 59 mL/minute/1.73 m$^2$) is a daily dose of 45 mg of dextromethorphan hydrobromide and 105 mg of bupropion hydrochloride, or a molar equivalent amount of another form of dextromethorphan and/or bupropion, such as administration of one tablet (or one dosage form containing 45 mg of dextromethorphan hydrobromide and 105 mg of bupropion hydrochloride) once daily, such as one tablet or other oral dosage form daily in the morning.

Patients who are concomitantly using the subject combination with strong CYP2D6 inhibitors may require special dosing. Concomitant use of the subject combination with a strong CYP2D6 inhibitor increases plasma concentrations of dextromethorphan. In some embodiments, the recommended dosage of the subject combination when coadministered with a strong CYP2D6 inhibitor is one tablet (or one dosage form containing 45 mg of dextromethorphan hydrobromide and 105 mg of bupropion hydrochloride) once daily, such as one tablet or other oral dosage form daily in the morning. In some embodiments, the patients are monitored for adverse reactions potentially attributable to dextromethorphan, such as somnolence and dizziness.

Patients who are known CYP2D6 poor metabolizers (PMs) may require special dosing. In some embodiments, the recommended dosage for patients known to be poor CYP2D6 metabolizers is one tablet (or one dosage form containing 45 mg of dextromethorphan hydrobromide and 105 mg of bupropion hydrochloride) once daily, such as one tablet or other oral dosage form daily in the morning.

Special precautions may be required when switching a patient to or from a monoamine oxidase inhibitor (MAOI) antidepressant to the subject combination. In some embodiments, at least 14 days must elapse between discontinuation of an MAOI intended to treat depression and initiation of therapy with the subject combination. Conversely, in some embodiments, at least 14 days must be allowed after stopping the subject combination before starting an MAOI antidepressant.

In the subject combination, bupropion inhibits the metabolism of dextromethorphan via CYP2D6. Dextromethorphan, when co-administered with bupropion, displays nonlinear pharmacokinetics at steady state, with greater than dose-proportional changes in AUC and $C_{max}$ for varying doses of dextromethorphan (30 to 60 mg) and less than dose-proportional changes for varying doses of bupropion (75 to 150 mg).

Steady state plasma concentrations of dextromethorphan and bupropion when given as the subject combination are achieved within 8 days. The accumulation ratios for dextromethorphan at steady state are about 20 and about 32, respectively based on $C_{max}$ and $AUC_{0-12}$. The accumulation ratios for bupropion at steady state are 1.1 and 1.5, respectively based on $C_{max}$ and $AUC_{0-12}$.

After administration of the subject combination, the median $T_{max}$ of dextromethorphan is about 3 hours and the median $T_{max}$ of bupropion is about 2 hours. The $C_{max}$ of hydroxybupropion metabolite occurs approximately 3 hours post-dose and is approximately 14 times the peak level of bupropion. The $AUC_{0-12}$ hydroxybupropion is about 19 times that of bupropion. The $C_{max}$ of the erythrohydroxybupropion and threohydroxybupropion metabolites occurs approximately 4 hours post-dose and is approximately equal to and about 5 times that of bupropion, respectively. The $AUC_{0-12}$ values of erythrohydroxybupropion and threohydroxybupropion are about 1.2 and about 7 times that of bupropion, respectively.

The subject combination can be taken with or without food. Dextromethorphan $C_{max}$ and $AUC_{0-12}$ were unchanged and decreased by 14%, respectively, and bupropion $C_{max}$ and $AUC_{0-12}$ were increased by 3% and 6%, respectively, when the subject combination was administered with food.

The plasma protein binding of dextromethorphan is approximately 60-70% and bupropion is 84%. The extent of protein binding of the hydroxybupropion metabolite is similar to that for bupropion; whereas the extent of protein binding of the threohydrobupropion metabolite is about half that seen with bupropion.

Following 8 days of administration of the subject combination in extensive metabolizers, the mean elimination half-life of dextromethorphan was increased approximately 3-fold to about 22 hours, as compared to dextromethorphan given without bupropion.

The mean elimination half-life of dextromethorphan and bupropion was 22 hours and 15 hours, respectively. The apparent elimination half-life of hydroxybupropion, erythrohydroxybuporpion and threohydroxybupropion metabolites were approximately 35, 44 and 33 hours, respectively.

Esketamine is a non-competitive NMDA receptor antagonist indicated, in conjunction with an oral antidepressant, for the treatment of treatment-resistant depression in adults. Treatment of treatment-resistant depression carries a risk of dissociation. The label for esketamine states that because of the risks of sedation and dissociation, patients must be monitored for at least 2 hours at each treatment session, followed by an assessment to determine when the patient is considered clinically stable and ready to leave the healthcare setting.

Dissociation includes: delusional perception; depersonalization/derealization disorder; derealization; diplopia; dissociation; dysesthesia; feeling cold; feeling hot; feeling of body temperature change; hallucination; hallucination, auditory; hallucination, visual; hyperacusis; illusion; ocular discomfort; oral dysesthesia; paranesthesia; paranesthesia oral; pharyngeal paranesthesia; photophobia; time perception altered; tinnitus; vision blurred; visual impairment.

The subject combination is a combination of dextromethorphan, an uncompetitive N-methyl D-aspartate (NDMA) receptor antagonist and sigma-1 receptor agonist, and bupropion, an aminoketone and CYP450 2D6 inhibitor, indicated for the treatment of major depressive disorder (MDD) in adults. Unlike esketamine, the subject combination can be administered as a without dissociation or dissociative events. In some embodiments, the patient is not monitored for dissociation after the subject combination is administered.

Unlike the combination of quinidine and dextromethorphan, at a dose of a combination of 105 mg of bupropion hydrochloride and 45 mg of dextromethorphan hydrobromide given twice a day, the subject combination does not prolong the QT interval to any clinically relevant extent. Thus, for a human patient who is experiencing major depressive disorder and is at risk of QT prolongation and torsades de pointer, electrocardiographic evaluation of QT interval is not typically conducted on the human patient.

The subject combination may be used for adjunctive treatment of major depressive disorder or depression.

In addition to major depressive disorder, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, Hitting (including self), Kicking, Grabbing onto people, Pushing, Throwing things, Biting, Scratching, Spitting, Hurting self or others, Tearing things or destroying property, Making physical sexual advances, Pacing, aimless wandering, Inappropriate dress or disrobing, Trying to get to a different place, Intentional falling, Eating/drinking inappropriate substances, Handling things inappropriately, Hiding things, Hoarding things, Performing repetitive mannerisms, General restlessness, Screaming, Making verbal sexual advances, Cursing or verbal aggression, Repetitive sentences or questions, Strange noises (weird laughter or crying), Complaining, Negativism, Constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandoff disease, and hereditary spastic paraplegia.

Neurodegenerative diseases that may be treated the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating", or "treatment" includes the diagnosis, cure, mitigation, treatment, or prevention of disease in man or other animals, or any activity that otherwise affects the structure or any function of the body of man or other animals.

A subject combination may be used to treat any disease or condition identified as treatable by the combination of bupropion and dextromethorphan in any of the following U.S. Pat. Nos. 8,569,328, 9,168,234, 9,198,905, 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

Example 1

In a study of the subject combination in 7 subjects with moderate (GFR 30-60 mL/min) renal impairment compared to 6 matched controls with normal renal function (matched in gender, age, and weight range to impaired subjects), both dextromethorphan and bupropion exposures increased by approximately 2-fold and clearances were reduced by 50%.

Example 2

Approximately 7 to 10% of Caucasians and 3 to 8% of African Americans lack the capacity to metabolize CYP2D6 substrates and are classified as poor metabolizers. In 3 poor metabolizers the pharmacokinetics of the subject combination resulted in an approximate 3-fold and 3.4-fold increase in dextromethorphan $C_{max}$ and $AUC_{0-12}$, respectively, compared to extensive metabolizers. An exploration of steady state pharmacokinetic data in 12 poor metabolizers treated with the subject combination in efficacy trials showed plasma concentrations of dextromethorphan that were generally higher than exposures for non-poor metabolizers.

Example 3

Co-administration of the SSRI paroxetine and the subject combination was studied in 29 healthy volunteers. Paroxetine increased the overall exposure of dextromethorphan by 2.5-fold and had no effect on bupropion. The overall exposure of paroxetine was increased by 1.2-fold when co-administered with the subject combination. Based on these results, when the subject combination is prescribed with drugs that inhibit CYP2D6, the subject combination should be dosed once daily. Use caution when administering the subject combination in conjunction with drugs which are extensively metabolized via CYP2D6.

Example 4

The properties of a tablet containing a combination of dextromethorphan hydrobromide, which is an uncompetitive NMDA receptor antagonist and sigma-1 receptor agonist, and bupropion hydrochloride, which is an aminoketone and CYP450 2D6 inhibitor, were studied.

The tablets are for oral administration and are round bilayer tablets. Each tablet contains 45 mg dextromethorphan hydrobromide (equivalent to 32.98 mg of the dextromethorphan free base) in an immediate-release formulation and 105 mg bupropion hydrochloride (equivalent to 91.14 mg of the bupropion free base) in an extended-release formulation. Each tablet contains the following inactive ingredients: carbomer homopolymer, colloidal silicon dioxide, crospovidone, glyceryl monocaprylocaprate, 1-cysteine hydrochloride monohydrate, magnesium stearate, microcrystalline cellulose, polyvinyl alcohol, red iron oxide, sodium lauryl sulfate, stearic acid, talc, titanium dioxide, and/or yellow iron oxide.

The effects of renal impairment, hepatic impairment, and CYP2D6 poor metabolizer status on the exposure to a tablet containing 45 mg of dextromethorphan hydrobromide and 105 mg of bupropion hydrochloride are summarized in FIG. 1

Results depicted in FIG. 1 are based on plasma concentrations in human patients after 8 days of twice daily dosing of a tablet containing 45 mg of dextromethorphan hydrobromide and 105 mg of bupropion hydrochloride. Data are GMRs and 90% CIs. Reference used are the matched healthy subjects for renal and hepatic impairment studies, and extensive or ultra-extensive CYP2D6 metabolizers. AUC represents the area under the plasma concentration-time curve from zero to 12 hours; BUP represents bupropion; CI is confidence interval; $C_{max}$ is maximum plasma concentration; DM represents dextromethorphan; GMRs represents geometric mean ratios; PK represents pharmacokinetics.

For patients having moderate renal impairment, a 2.21-fold increase in dextromethorphan $AUC_{0-12}$, a 2.10-fold increase in dextromethorphan $C_{max}$, a 1.80-fold increase in bupropion $AUC_{0-12}$, and a 1.87-fold increase in bupropion $C_{max}$ were observed.

Based upon these results, dosage adjustment is recommended in patients known to have moderate renal impairment because these patients have higher dextromethorphan and bupropion concentrations than patients with healthy renal function. The recommended total daily dose for patients known to have moderate renal impairment is about 45 mg of dextromethorphan hydrobromide and about 105 mg of bupropion hydrochloride (e.g., one tablet containing about 45 mg of dextromethorphan hydrobromide and about 105 mg of bupropion hydrochloride for administration once daily, such as in the morning), or an equivalent dose of another form dextromethorphan and/or bupropion.

The invention claimed is:

1. A method of treating major depressive disorder in a human patient who has moderate renal impairment, comprising administering once daily, by mouth, one tablet containing about 105 mg of bupropion hydrochloride and about 45 mg of dextromethorphan hydrobromide to the human patient who has moderate renal impairment and is experiencing major depressive disorder, wherein the dextromethorphan hydrobromide is in an immediate-release formulation, wherein the bupropion hydrochloride is in an extended-release formulation, and wherein the tablet is a bilayer tablet.

2. A method of treating major depressive disorder in a human patient who has moderate renal impairment, comprising administering once daily, by mouth, one tablet containing about 105 mg of bupropion hydrochloride and about 45 mg of dextromethorphan hydrobromide to the human patient who has moderate renal impairment and is experiencing major depressive disorder, wherein the dextromethorphan hydrobromide is in an immediate-release formulation, wherein the bupropion hydrochloride is in an extended-release formulation, and wherein the $T_{max}$ of dextromethorphan is about 3 hours.

3. The method of claim 2, wherein steady state plasma concentrations of dextromethorphan and bupropion are achieved within 8 days, and wherein the accumulation ratio for dextromethorphan at steady state is about 20 based on the $C_{max}$.

4. The method of claim 2, wherein steady state plasma concentrations of dextromethorphan and bupropion are achieved within 8 days, and wherein the accumulation ratio for dextromethorphan is about 32 based on the $AUC_{0-12}$.

5. The method of claim 2, wherein the once-daily administration avoids the human patient having an about 2.2-fold increase in $AUC_{0-12}$ of dextromethorphan as compared to the $AUC_{0-12}$ of dextromethorphan that would result from twice daily administration of the tablet for 8 days to a human patient who has no renal impairment.

6. The method of claim 2, wherein the once-daily administration avoids the patient having an about 2.1-fold increase in $C_{max}$ of dextromethorphan as compared to the $C_{max}$ of dextromethorphan that would result from twice daily administration of the tablet for 8 days to a human patient who has no renal impairment.

7. The method of claim 2, wherein the once-daily administration avoids the human patient having an about 1.8-fold increase in $AUC_{0-12}$ of bupropion as compared to the $AUC_{0-12}$ of bupropion that would result from twice daily administration of the tablet for 8 days to a human patient who has no renal impairment.

8. The method of claim 2, wherein the once-daily administration avoids the patient having an about 1.9-fold increase in $C_{max}$ of bupropion as compared to the $C_{max}$ of bupropion that would result from twice daily administration of the tablet for 8 days to a human patient who has no renal impairment.

9. A method of treating major depressive disorder in a human patient who has moderate renal impairment, comprising administering a daily dose of: (i) about 105 mg of bupropion hydrochloride and (ii) about 45 mg of dextromethorphan hydrobromide to the human patient who has moderate renal impairment and is experiencing major depressive disorder, and wherein the human patient has an estimated glomerular filtration rate that is between about 30 mL/min/1.72 m$^2$ and 59 mL/min/1.72 m$^2$.

10. The method of claim 9, wherein the administering is achieved by once daily administration, by mouth, of one tablet containing about 105 mg of bupropion hydrochloride and about 45 mg of dextromethorphan hydrobromide.

11. The method of claim 10, wherein the dextromethorphan hydrobromide is in an immediate-release formulation.

12. The method of claim 11, wherein the bupropion hydrochloride is in an extended-release formulation.

13. The method of claim 12, wherein the tablet is a bilayer tablet.

14. The method of claim 12, wherein the $T_{max}$ of dextromethorphan is about 3 hours.

15. The method of claim 12, wherein steady state plasma concentrations of dextromethorphan and bupropion are achieved within 8 days, and wherein the accumulation ratio for dextromethorphan at steady state is about 20 based on the $C_{max}$.

16. The method of claim 12, wherein steady state plasma concentrations of dextromethorphan and bupropion are achieved within 8 days, and wherein the accumulation ratio for dextromethorphan at steady state is about 32 based on the $AUC_{0-12}$.

17. The method of claim 12, wherein the once-daily administration avoids the human patient having an about 2.2-fold increase in $AUC_{0-12}$ of dextromethorphan as compared to the $AUC_{0-12}$ of dextromethorphan that would result from twice daily administration of the tablet for 8 days to a human patient who has no renal impairment.

18. The method of claim 12, wherein the once-daily administration avoids the patient having an about 2.1-fold increase in $C_{max}$ of dextromethorphan as compared to the $C_{max}$ of dextromethorphan that would result from twice daily administration of the tablet for 8 days to a human patient who has no renal impairment.

19. The method of claim 12, wherein the once-daily administration avoids the human patient having an about 1.8-fold increase in $AUC_{0-12}$ of bupropion as compared to the $AUC_{0-12}$ of bupropion that would result from twice daily administration of the tablet for 8 days to a human patient who has no renal impairment.

20. The method of claim 12, wherein the once-daily administration avoids the patient having an about 1.9-fold increase in $C_{max}$ of bupropion as compared to the $C_{max}$ of bupropion that would result from twice daily administration of the tablet for 8 days to a human patient who has no renal impairment.

* * * * *

UNITED STATES PATENT AND TRADEMARK OFFICE
CERTIFICATE OF CORRECTION

PATENT NO. : 11,730,706 B1
APPLICATION NO. : 18/158268
DATED : August 22, 2023
INVENTOR(S) : Herriot Tabuteau It is certified that error appears in the above-identified patent and that said Letters Patent is hereby corrected as shown below:

In the Claims

Column 12, Line 15: Claim 9, replace "mL/minute/1.72 $m^2$ and 59 mL/minute/1.72 $m^2$" with --mL/minute/1.73 $m^2$ and 59 mL/minute/1.73 $m^2$--

Signed and Sealed this
Twenty-fifth Day of June, 2024

Katherine Kelly Vidal
*Director of the United States Patent and Trademark Office*